(12) United States Patent
Boyle, Jr. et al.

(10) Patent No.: US 8,048,233 B2
(45) Date of Patent: Nov. 1, 2011

(54) METHODS AND DEVICES TO CLEAR OBSTRUCTIONS FROM MEDICAL TUBES

(75) Inventors: Edward M. Boyle, Jr., Bend, OR (US); Nathan J. Dale, Bothell, WA (US); Paul C. Leonard, Woodinville, WA (US); Alan Marc Gillinov, Orange Village, OH (US); Sam Kiderman, Broadview Heights, OH (US); William E. Cohn, Bellaire, TX (US)

(73) Assignees: Clear Catheter Systems, Inc., Bend, OR (US); The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 12/915,328

(22) Filed: Oct. 29, 2010

(65) Prior Publication Data
US 2011/0040286 A1    Feb. 17, 2011

Related U.S. Application Data

(63) Continuation of application No. 12/359,826, filed on Jan. 26, 2009.

(60) Provisional application No. 61/189,850, filed on Aug. 22, 2008, provisional application No. 61/023,829, filed on Jan. 25, 2008.

(51) Int. Cl.
*B08B 9/04* (2006.01)
*B08B 9/055* (2006.01)
*B08B 1/00* (2006.01)

(52) U.S. Cl. ............... 134/22.11; 134/8; 134/166 C; 15/104.05; 604/540; 604/541; 604/544; 604/318; 606/159; 606/127; 606/106

(58) Field of Classification Search ............ 134/8, 22.11, 134/166 C; 15/104.05; 604/540, 541, 544, 604/318; 606/159, 127, 106
See application file for complete search history.

(56) References Cited

U.S. PATENT DOCUMENTS

| 3,416,532 | A | 12/1968 | Grossman |
| 3,946,741 | A | 3/1976 | Adair |
| 3,957,054 | A | 5/1976 | McFarlane |

(Continued)

FOREIGN PATENT DOCUMENTS

WO    94/03226 A1    2/1994

(Continued)

OTHER PUBLICATIONS

International Search Report and Written Opinion issued Dec. 16, 2009 in related PCT Application No. PCT/US09/32000.

(Continued)

*Primary Examiner* — Michael Kornakov
*Assistant Examiner* — Natasha Campbell
(74) *Attorney, Agent, or Firm* — Pearne & Gordon LLP

(57) ABSTRACT

A device for clearing obstructions from a medical tube, such as a chest tube, is disclosed in various embodiments. The device features a clearance member in the form of a loop. The loop desirably has a diameter that substantially corresponds to the inner diameter of the medical tube. Also desirably, the loop presents a substantially unobstructed pathway therethrough for the flow of material from a location in the medical tube distal to the loop to a location in the medical tube proximal to the loop regardless whether the clearance member is being translated or is at rest in the medical tube. Methods of utilizing such a device are also disclosed.

22 Claims, 15 Drawing Sheets

U.S. PATENT DOCUMENTS

| | | | |
|---|---|---|---|
| 3,991,762 A | 11/1976 | Radford | |
| 4,006,743 A | 2/1977 | Kowarski | |
| 4,148,319 A | 4/1979 | Kasper | |
| 4,228,802 A | 10/1980 | Trott | |
| 4,257,422 A | 3/1981 | Duncan | |
| 4,317,452 A | 3/1982 | Russo et al. | |
| 4,324,262 A | 4/1982 | Hall | |
| 4,429,693 A | 2/1984 | Blake et al. | |
| 4,445,897 A | 5/1984 | Ekbladh | |
| 4,465,481 A | 8/1984 | Blake | |
| 4,523,920 A | 6/1985 | Russo | |
| 4,569,344 A | 2/1986 | Palmer | |
| 4,638,539 A | 1/1987 | Palmer | |
| 4,692,153 A | 9/1987 | Berlin et al. | |
| 4,696,296 A | 9/1987 | Palmer | |
| 4,698,058 A | 10/1987 | Greenfeld et al. | |
| 4,706,671 A | 11/1987 | Weinrib | |
| 4,723,549 A | 2/1988 | Wholey et al. | |
| 4,728,319 A | 3/1988 | Masch | |
| 4,762,125 A | 8/1988 | Leiman et al. | |
| 4,771,772 A | 9/1988 | DeWitt | |
| 4,781,678 A | 11/1988 | de Couet et al. | |
| 4,865,030 A | 9/1989 | Polyak | |
| 4,865,586 A | 9/1989 | Hedberg | |
| 4,889,106 A * | 12/1989 | Watanabe | 600/101 |
| 4,909,781 A | 3/1990 | Husted | |
| 4,921,488 A | 5/1990 | Maitz | |
| 4,950,232 A | 8/1990 | Ruzicka | |
| 4,967,743 A | 11/1990 | Lambert | |
| 5,009,659 A | 4/1991 | Hamlin et al. | |
| 5,062,835 A | 11/1991 | Maitz | |
| 5,073,164 A | 12/1991 | Hollister et al. | |
| 5,215,522 A | 6/1993 | Page | |
| 5,240,675 A | 8/1993 | Wilk | |
| 5,260,020 A | 11/1993 | Wilk | |
| 5,261,877 A | 11/1993 | Fine | |
| 5,297,310 A | 3/1994 | Cox et al. | |
| 5,336,177 A | 8/1994 | Marcus | |
| 5,349,950 A | 9/1994 | Ulrich et al. | |
| 5,370,610 A | 12/1994 | Reynolds | |
| 5,490,503 A | 2/1996 | Hollister | |
| 5,505,713 A | 4/1996 | Van Antwerp | |
| 5,522,801 A | 6/1996 | Wang | |
| 5,536,248 A | 7/1996 | Weaver et al. | |
| 5,538,511 A | 7/1996 | Van Antwerp | |
| 5,599,299 A | 2/1997 | Weaver et al. | |
| 5,599,300 A | 2/1997 | Weaver et al. | |
| 5,630,823 A | 5/1997 | Schmitz-Rode | |
| 5,693,011 A | 12/1997 | Onik | |
| 5,715,815 A | 2/1998 | Lorenzen et al. | |
| 5,768,741 A * | 6/1998 | Leiman et al. | 15/304 |
| 5,772,261 A | 6/1998 | Magram | |
| 5,788,678 A | 8/1998 | Van Antwerp | |
| 5,788,681 A | 8/1998 | Weaver et al. | |
| 5,788,710 A | 8/1998 | Bates | |
| 5,807,330 A | 9/1998 | Teitelbaum | |
| 5,830,127 A | 11/1998 | DeCastro | |
| 5,843,028 A | 12/1998 | Weaver et al. | |
| 5,868,720 A | 2/1999 | Van Antwerp | |
| 5,895,398 A | 4/1999 | Wensel et al. | |
| 5,897,534 A | 4/1999 | Heim et al. | |
| 5,911,710 A | 6/1999 | Barry et al. | |
| 5,911,734 A | 6/1999 | Tsugita et al. | |
| 5,913,852 A | 6/1999 | Magram | |
| 5,921,952 A | 7/1999 | Desmond et al. | |
| 5,931,821 A | 8/1999 | Weilbacher et al. | |
| 5,957,932 A | 9/1999 | Bates et al. | |
| 5,964,223 A | 10/1999 | Baran | |
| 6,045,623 A | 4/2000 | Cannon | |
| 6,080,170 A | 6/2000 | Nash et al. | |
| 6,082,361 A | 7/2000 | Morejon | |
| 6,129,697 A | 10/2000 | Drasler et al. | |
| 6,168,603 B1 | 1/2001 | Leslie et al. | |
| 6,183,450 B1 | 2/2001 | Lois | |
| 6,248,100 B1 | 6/2001 | de Toledo et al. | |
| 6,264,624 B1 | 7/2001 | Desmond, III et al. | |
| 6,299,604 B1 | 10/2001 | Ragheb et al. | |
| 6,383,196 B1 | 5/2002 | Leslie et al. | |
| 6,436,112 B2 | 8/2002 | Wensel | |
| 6,454,775 B1 | 9/2002 | Demarais et al. | |
| 6,485,497 B2 | 11/2002 | Wensel et al. | |
| 6,508,789 B1 | 1/2003 | Sinnott et al. | |
| 6,514,273 B1 | 2/2003 | Voss | |
| 6,530,935 B2 | 3/2003 | Wensel et al. | |
| 6,547,761 B2 | 4/2003 | Liu | |
| 6,562,024 B2 | 5/2003 | Alvarez de Toledo et al. | |
| 6,582,400 B1 | 6/2003 | Hawk et al. | |
| 6,629,956 B1 | 10/2003 | Polidoro et al. | |
| 6,638,253 B2 | 10/2003 | Breznock | |
| 6,660,014 B2 | 12/2003 | Demarais et al. | |
| 6,663,650 B2 | 12/2003 | Sepetka et al. | |
| 6,679,262 B1 | 1/2004 | Morejon | |
| 6,692,459 B2 | 2/2004 | Teitelbaum | |
| 6,692,508 B2 | 2/2004 | Wensel et al. | |
| 6,692,509 B2 | 2/2004 | Wensel et al. | |
| 6,699,331 B1 | 3/2004 | Kritzler | |
| 6,702,830 B1 | 3/2004 | Demarais et al. | |
| 6,730,104 B1 | 5/2004 | Sepetka et al. | |
| 6,740,096 B2 | 5/2004 | Teague et al. | |
| 6,767,338 B2 | 7/2004 | Hawk et al. | |
| 6,780,193 B2 | 8/2004 | Leslie et al. | |
| 6,783,536 B2 | 8/2004 | Vilsmeier et al. | |
| 6,824,545 B2 | 11/2004 | Sepetka et al. | |
| 6,849,061 B2 | 2/2005 | Wagner | |
| 6,866,657 B2 | 3/2005 | Shchervinsky | |
| 6,893,418 B2 | 5/2005 | Liu | |
| 6,893,424 B2 | 5/2005 | Shchervinsky | |
| 6,905,484 B2 | 6/2005 | Buckman et al. | |
| 6,945,977 B2 | 9/2005 | Demarais et al. | |
| 7,004,954 B1 | 2/2006 | Voss | |
| 7,101,380 B2 | 9/2006 | Khachin et al. | |
| 7,125,402 B1 | 10/2006 | Yarger | |
| 7,135,010 B2 | 11/2006 | Buckman et al. | |
| 7,141,038 B2 | 11/2006 | Whalen et al. | |
| 7,211,067 B2 | 5/2007 | Hawk et al | |
| 7,229,433 B2 | 6/2007 | Mullen | |
| 7,241,287 B2 | 7/2007 | Shehada et al. | |
| 7,241,299 B2 | 7/2007 | Gerard | |
| 7,244,251 B2 | 7/2007 | Shehada et al. | |
| 7,252,659 B2 | 8/2007 | Shehada et al. | |
| 7,264,616 B2 | 9/2007 | Shehada et al. | |
| 7,267,671 B2 | 9/2007 | Shehada | |
| 7,285,126 B2 | 10/2007 | Sepetka et al. | |
| 7,326,197 B2 | 2/2008 | Breznock | |
| 7,338,478 B2 | 3/2008 | Leiboff | |
| 7,338,501 B2 | 3/2008 | Teague et al. | |
| 7,419,483 B2 | 9/2008 | Shehada | |
| 7,610,106 B2 | 10/2009 | Yacoubian | |
| 7,695,467 B2 | 4/2010 | Breznock et al. | |
| 7,799,046 B2 | 9/2010 | White et al. | |
| 7,811,293 B2 | 10/2010 | Simpson et al. | |
| 7,854,728 B2 | 12/2010 | Boyle, Jr. | |
| 2001/0018572 A1 | 8/2001 | Kinsey et al. | |
| 2002/0058915 A1 | 5/2002 | Wakabayashi | |
| 2002/0128601 A1 | 9/2002 | Reilly et al. | |
| 2003/0069551 A1 | 4/2003 | Bradley et al. | |
| 2003/0216760 A1 | 11/2003 | Welch et al. | |
| 2004/0006331 A1 | 1/2004 | Shchervinsky | |
| 2004/0073243 A1 | 4/2004 | Sepetka et al. | |
| 2004/0078026 A1 | 4/2004 | Wagner | |
| 2004/0092956 A1 | 5/2004 | Liddicoat et al. | |
| 2004/0181191 A1 | 9/2004 | Teitelbaum | |
| 2004/0219028 A1 | 11/2004 | Demarais et al. | |
| 2004/0230132 A1 | 11/2004 | Shehada | |
| 2005/0033348 A1 | 2/2005 | Sepetka et al. | |
| 2005/0055033 A1 | 3/2005 | Leslie | |
| 2005/0059995 A1 | 3/2005 | Sepetka et al. | |
| 2005/0085849 A1 | 4/2005 | Sepetka et al. | |
| 2005/0125024 A1 | 6/2005 | Sepetka et al. | |
| 2005/0154373 A1 | 7/2005 | Deutsch | |
| 2005/0171478 A1 | 8/2005 | Selmon et al. | |
| 2005/0171566 A1 | 8/2005 | Kanamaru | |
| 2005/0216030 A1 | 9/2005 | Sepetka et al. | |
| 2005/0216050 A1 | 9/2005 | Sepetka et al. | |
| 2005/0228363 A1 | 10/2005 | Leiboff | |
| 2005/0228417 A1 | 10/2005 | Teitelbaum | |
| 2005/0288686 A1 | 12/2005 | Sepetka et al. | |

| | | |
|---|---|---|
| 2006/0004404 A1 | 1/2006 | Khachin et al. |
| 2006/0142697 A1 | 6/2006 | Hawk et al. |
| 2006/0167416 A1 | 7/2006 | Mathis et al. |
| 2006/0195069 A1 | 8/2006 | Opie |
| 2006/0195137 A1 | 8/2006 | Sepetka et al. |
| 2006/0206097 A1 | 9/2006 | Breznock |
| 2006/0264974 A1 | 11/2006 | Khachin |
| 2006/0264988 A1 | 11/2006 | Boyle |
| 2007/0032779 A1 | 2/2007 | Accisano |
| 2007/0049904 A1 | 3/2007 | Deutsch |
| 2007/0078389 A1 | 4/2007 | Whalen et al. |
| 2007/0083189 A1 | 4/2007 | Lampropoulos et al. |
| 2007/0135795 A1 | 6/2007 | De Paulis |
| 2007/0149946 A1 | 6/2007 | Viswanathan |
| 2007/0179513 A1 | 8/2007 | Deutsch |
| 2007/0198030 A1 | 8/2007 | Martin et al. |
| 2007/0208371 A1 | 9/2007 | French et al. |
| 2007/0288036 A1 | 12/2007 | Seshadri et al. |
| 2008/0045881 A1 | 2/2008 | Teitelbaum |
| 2008/0051720 A1 | 2/2008 | Nash et al. |
| 2008/0091146 A1 | 4/2008 | Solovay et al. |
| 2008/0109032 A1 | 5/2008 | Sepetka et al. |
| 2008/0119869 A1 | 5/2008 | Teague et al. |
| 2008/0177276 A1 | 7/2008 | Teague et al. |
| 2008/0177296 A1 | 7/2008 | Sepetka et al. |
| 2008/0183197 A1 | 7/2008 | Sepetka et al. |
| 2008/0183198 A1 | 7/2008 | Sepetka et al. |
| 2008/0183205 A1 | 7/2008 | Sepetka et al. |
| 2008/0188876 A1 | 8/2008 | Sepetka et al. |
| 2008/0188885 A1 | 8/2008 | Sepetka et al. |
| 2008/0215077 A1 | 9/2008 | Sepetka et al. |
| 2008/0234706 A1 | 9/2008 | Sepetka et al. |
| 2009/0062772 A1 | 3/2009 | Wakeford et al. |
| 2009/0188531 A1 | 7/2009 | Boyle, Jr. et al. |
| 2009/0264833 A1 | 10/2009 | Boyle, Jr. |
| 2009/0326513 A1 | 12/2009 | Deutsch et al. |
| 2011/0040285 A1 | 2/2011 | Boyle, Jr. |

FOREIGN PATENT DOCUMENTS

| | | |
|---|---|---|
| WO | 2004/108051 A2 | 12/2004 |
| WO | 2005/067647 A2 | 7/2005 |
| WO | 2006/071855 A2 | 7/2006 |
| WO | 2006/074283 A2 | 7/2006 |
| WO | 2007/090057 A2 | 8/2007 |
| WO | 2007/098376 A2 | 8/2007 |

OTHER PUBLICATIONS

International Search Report and Written Opinion issued Jan. 13, 2010 in PCT Application No. PCT/US09/45954.

International Search Report issued Oct. 22, 2003 and International Preliminary Examination Report issued Aug. 16, 2004 in PCT Application No. PCT/US01/45648 .

International Search Report and Written Opinion issued Nov. 19, 2004 in PCT Application No. PCT/US04/13728.

Supplementary Partial European Search Report dated Apr. 11, 2006 in European Patent Application No. 01986082.4.

* cited by examiner

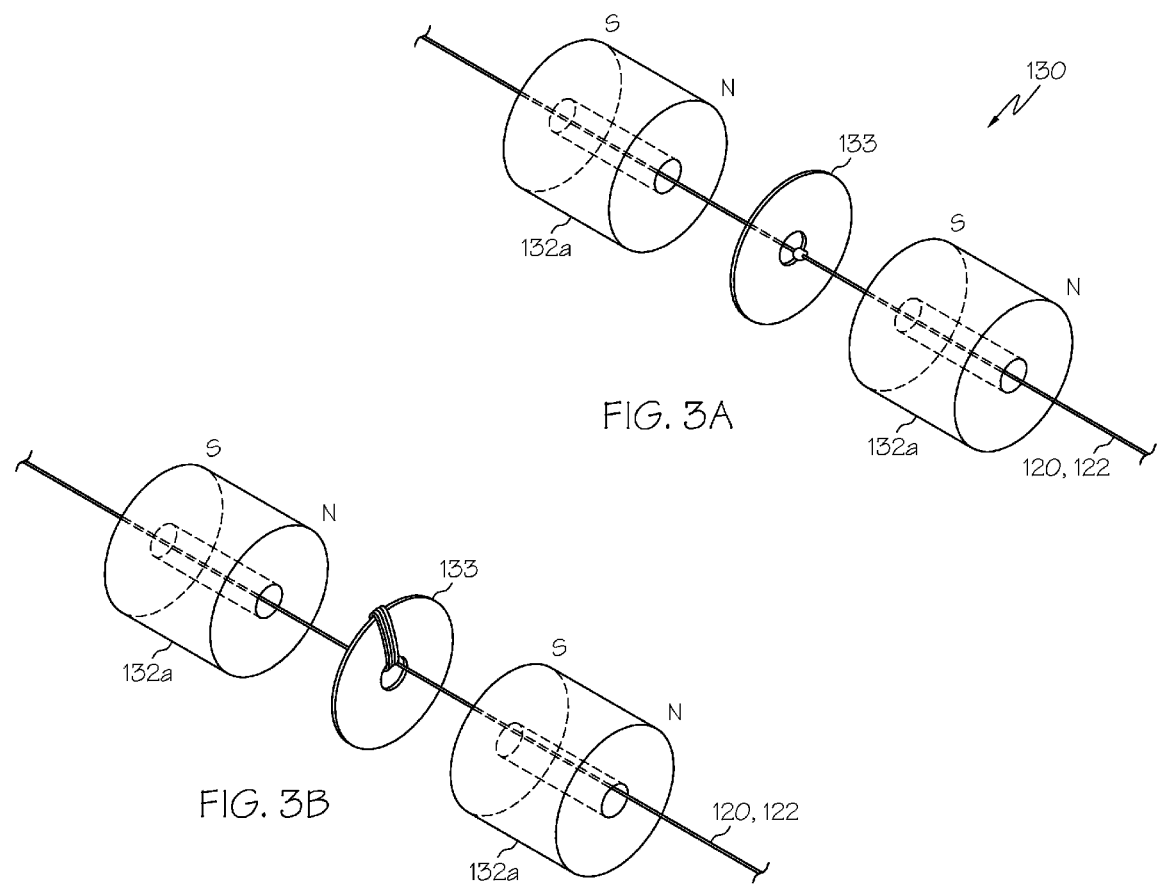

METHODS AND DEVICES TO CLEAR OBSTRUCTIONS FROM MEDICAL TUBES

CROSS-REFERENCE TO RELATED APPLICATIONS

This application is a continuation of U.S. patent application Ser. No. 12/359,826 filed Jan. 26, 2009, which claims the benefit of U.S. provisional patent application Ser. No. 61/189,850 filed Aug. 22, 2008, and U.S. provisional patent application Ser. No. 61/023,829 filed Jan. 25, 2008. The contents of all the foregoing applications are incorporated herein by reference.

BACKGROUND

1. Field of the Invention

The invention relates to methods and devices to clear obstructive debris from medical tubes. More particularly, it relates to such a device having a clearance member that can be actuated to draw such debris proximally in a medical tube without compromising the sterile field.

2. Description of Related Art

Millions of medical tubes are used every year to drain bodily fluids and secretions from within body orifices. For example, such tubes can be used to drain fluid from one's bladder, from the colon or other portions of the alimentary tract, or from the lungs or other organs in conjunction with various therapies. Medical tubes also are used to drain blood and other fluids that typically accumulate within the body cavity following traumatic surgery. In all these cases, a tube is inserted into the patient so that its terminal end is provided in or adjacent the space where it is desired to remove accumulated or pooled fluid, and the proximal end remains outside the patient's body, where it is typically connected to a suction source.

One of the biggest categories of patients requiring medical tube drainage is patients who have had heart and lung surgery, nearly all of whom require at least one chest tube to drain the space around the heart and lungs after surgery. Chest tubes are long, usually semi-stiff, plastic tubes that are inserted into the chest in the vicinity of the heart and lungs to drain collections of fluids or air from within the pleura, the mediastinum or pericardial space, or from within the thoracic cavity generally.

In all cases, fluid and other material accumulating in the vicinity of the medical tube's distal end (within the patient) is drawn through that tube and out of the space where it accumulated via suction applied at the tube's proximal end. Ideally, the medical tube will remain free from clots and other debris that may partially or totally obstruct the suction pathway within the medical tube. Unfortunately, however, bodily secretions (particularly those including blood or blood platelets) often form clots within medical tubes, which can partially or totally obstruct the suction pathway within the tube.

Obstruction of a medical tube can impact its effectiveness to remove the fluid and other material for which it was originally placed, eventually rendering the medical tube partially or totally non-functional. In some cases, a non-functional tube can have serious or potentially life-threatening consequences. For example, if there is a blockage in a chest tube following cardiac or pulmonary surgery, the resulting accumulation of fluid around the heart and lungs without adequate drainage can cause serious adverse events such as pericardial tamponade and pneumothorax. In addition to chest tubes used in heart, lung and trauma surgery, other medical tubes are prone to clogging as well, including feeding tubes, surgical wound drains, urinary catheters, cardiovascular catheters and others.

There are few effective techniques to manage medical tube clogging when it occurs. During the perioperative period following chest surgery or trauma, clinicians will undertake measures to try to remove any debris (such as a clot) that has accumulated or formed within the chest tube, to keep the tube clear. One method is to simply tap the tube to try and break up the debris. Another method is referred to as 'milking the tube.' 'Milking' involves using one's fingers, or a rudimentary device composed of a pair of pliers with rollers fashioned onto its jaws, to compress the tube over the debris to try and break it up. The goal is to loosen the debris, or to break it into smaller pieces, so it can be more readily drawn out of the tube via suction applied at the proximal end.

Another technique is fan folding. In this technique, the clinician bends the chest tube in various ways to try to break up any long clots or other obstructions that extend along the axis of the medical tube. The aim is to produce several smaller pieces of debris, as opposed to one long piece, that will be more readily drawn proximally via the suction applied at the tube's proximal end. Still another technique is known as 'stripping.' Here, the clinician takes two fingers lubricated in some fashion, or the improvised device composed of a pair of pliers with rollers mentioned above, and 'strips' the tube. This is achieved by compressing the tube initially near where it enters the patient, and drawing the compressing apparatus (one's fingers or other compression device) proximally, with compression still applied, along the tube's length toward the suction source. This is done repeatedly to try and work any obstructive debris out from the tube and toward the suction source.

None of the above techniques is particularly effective. Moreover, they are time consuming and can be quite painful if the patient is awake and alert when they are performed, due to tugging on the medical tube. Tugging on chest tubes whose terminal ends have been placed near the pleura or pericardium can be especially painful. In addition, the 'stripping' technique is known to generate short bursts of extreme negative pressure within chest tubes, which in turn draws a strong suction in the body cavity where its terminal end has been placed. This can be quite dangerous in certain circumstances. For example, negative pressures of magnitude greater than −300 cm of water can be generated adjacent suture lines on coronary anastomosis, etc., which can disrupt some of the work that was done during a prior surgery. As a result, many surgeons have banned stripping their patients' chest tubes due to the potential for complications.

When the above techniques fail to clear a potentially dangerous clot within the tube, a more invasive technique must be used. This requires establishment of a sterile field around the chest tube, which is disconnected from the suction source to manually insert a suction catheter to clear the debris. This is known as open chest tube suctioning, and it can be effective to clear a clogged chest tube. But it is highly undesirable for a number of reasons. First, it compromises the sterile field within the chest tube system by exposing the internal environment within that system to the external environment, potentially introducing bacteria inside the chest. Second, the closed system (suction source to chest tube to body space within the chest) typically must be breached to insert the catheter inside the chest tube. Breaking the seal on this system causes loss of the normal physiologic negative pressure inside the chest. This can result in lung collapse (pneumothorax) while suctioning the chest tube. Additionally, the suction catheter can easily be passed beyond the end of the chest tube, which has the potential to injure the heart or lungs, which could be life threatening. Finally, this procedure is time consuming and usually can only be performed by physicians due to the associated dangers. Thus it is only occasionally done in extreme situations when a clogged chest tube is causing a serious acute problem.

Currently, surgeons often implant two or more medical tubes, or employ large-diameter tubes, following surgery to provide additional drainage capacity and avoid potentially life-threatening complications of a clogged tube. Methods and apparatus are desirable to keep medical tubes from clogging or to clear them reliably without having to breach the closed system between the suction source and the body cavity requiring drainage. Such methods/apparatus may allow surgeons to place fewer tubes post-surgery, or to select tubes having smaller diameters, both of which will reduce patient discomfort and recovery time. Placement of fewer tubes also will minimize the risk of infection.

SUMMARY OF THE INVENTION

A device for clearing obstructions from a medical tube includes a shuttle guide tube having an inner diameter, a shuttle member disposed outside the guide tube and adapted to translate along a length thereof, an elongate guide member, a clearance member attached to or formed integrally with the guide member, and a magnetic guide secured to the guide member. The magnetic guide is adapted to be magnetically coupled to the shuttle member through a wall of the guide tube so that translation of the shuttle member along the length thereof induces a corresponding translation of the guide wire.

A method of clearing obstructions from a medical tube includes coupling a shuttle guide tube with a medical tube, and translating a shuttle member disposed outside the guide tube along a length thereof to correspondingly translate an elongate guide member that is at least partially disposed within the guide tube and magnetically coupled to the shuttle member through a wall of the guide tube. This correspondingly translates a clearance member attached to or formed with the guide member through the medical tube.

Another method of clearing obstructions from a medical tube includes coupling a shuttle guide tube with a medical tube, thereby defining a sterile field within the respective tubes, and translating a shuttle member disposed outside the guide tube along a length thereof to correspondingly translate an elongate guide member that is at least partially disposed within the guide tube without compromising the sterile field, thereby correspondingly translating a clearance member attached to or formed with said guide member through the medical tube.

A chest-tube assembly includes a chest tube, a clearance device adapted to couple with and dislodge debris accumulated within the chest tube, and a $CO_2$ sensor provided in fluid communication with the chest tube to sense the presence of $CO_2$ in the chest tube.

BRIEF DESCRIPTION OF THE DRAWINGS

FIGS. 3a-3d illustrate various embodiments of a magnetic guide as hereafter described, as well as various modes of attachment thereof to a guide wire.

DETAILED DESCRIPTION OF PREFERRED EMBODIMENTS

As used herein, the terms proximal and distal are generally to be construed with reference to a patient that has been or is to be fitted with a medical tube, such as a chest tube. For example, the distal end or region of a medical tube (e.g. chest tube) is that end or region that is to be inserted into or disposed more adjacent (e.g. within) the patient during use, as compared to the opposite end or region of the medical tube (chest tube). Similarly, a distal element (or the distal side or region of an element) is nearer to the patient, or to the distal end of the chest tube, than a proximal element (or the proximal side or region of an element). Also herein, the "terminal" end of a tube, wire or member refers to its distal end.

Figure 1:
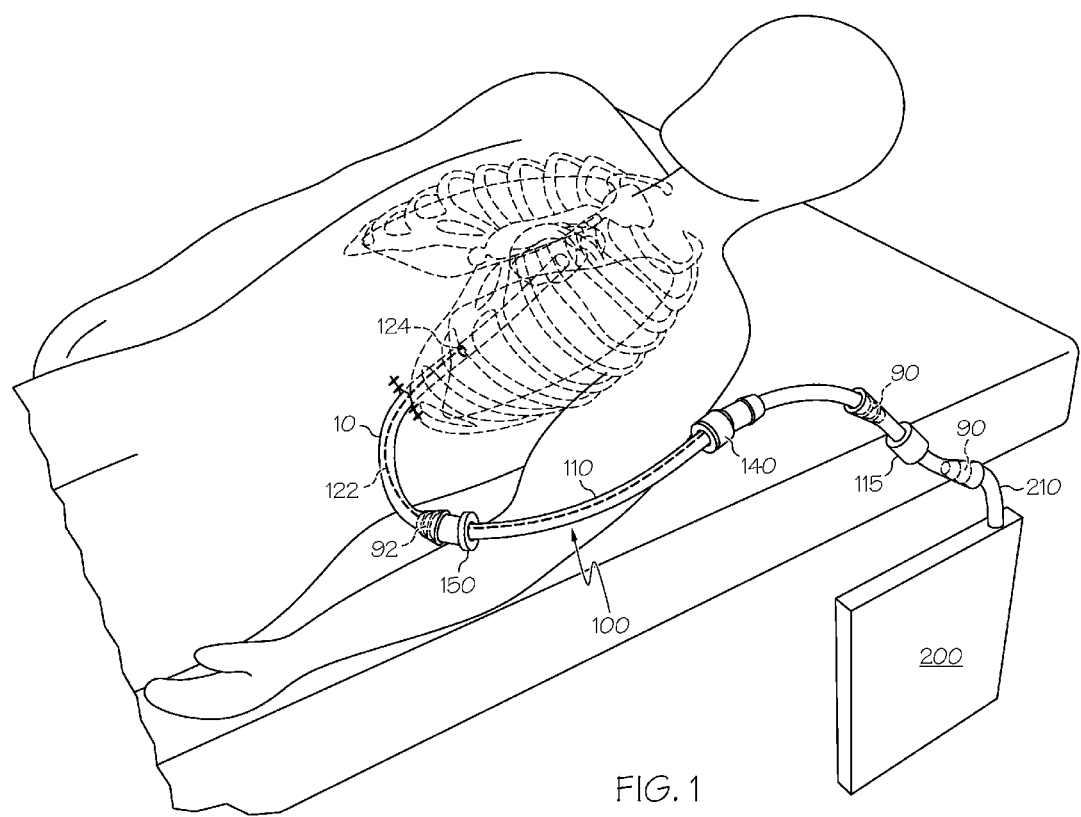
FIG. 1 is a schematic perspective illustration showing a clearance device coupled to a medical tube (chest tube) that has been placed in a patient recovering from surgery, to permit clearance of the medical tube of obstructions formed therein.

FIG. 1 shows a schematic representation of a medical tube being used to drain accumulated fluid from within the body cavity of a patient, in accordance with an exemplary embodiment of the invention. In FIG. 1 the medical tube is inserted into and used to drain fluid from the chest cavity of the patient, and so is referred to as a chest tube 10. Chest tubes 10 are a common type of medical drain tube and the remaining description will be provided with reference to chest tubes 10. However, it is to be appreciated that the aspects and embodiments of the invention hereafter described can be applied directly or with minor and routine modifications to clear obstructive debris from different medical tubes used in different applications, for example catheters, surgical drain tubes to drain fluid from other orifices (besides the chest cavity), endotrachial tubes, feeding tubes, gastric tubes or tubes to deliver material to or from the alimentary tract, etc.

Returning to FIG. 1, the chest tube 10 enters the patient through the chest-cavity (body) wall, so that its distal end is positioned within the chest (body) at a location from which fluid is to be drained. The proximal end of the chest tube 10 remains outside the body. The chest tube 10 can be inserted into the patient in a conventional manner, and positioned and secured in place through the chest-cavity wall by the physician. A clearance device 100 is fitted to the proximal end of the chest tube 10. The clearance device 100 includes a shuttle guide tube 110 (described below) that is connected to the proximal end of the chest tube 10 and is provided in fluid communication therewith. The clearance device also includes a clearance member 124 that can be reversibly advanced into and through the chest tube 10 to withdraw obstructive debris therefrom (also described below). The proximal end of the shuttle guide tube 110 (i.e. the end opposite the point of connection to the chest tube 10) is connected to a suction source 200, e.g. via a suction tube 210. The suction source draws a suction within the chest tube 10, via the shuttle guide tube 110 and suction tube 210 (if present), both to draw fluid out of the body cavity and also to sustain the normal physiologic negative pressure within the chest.

Figure 2:
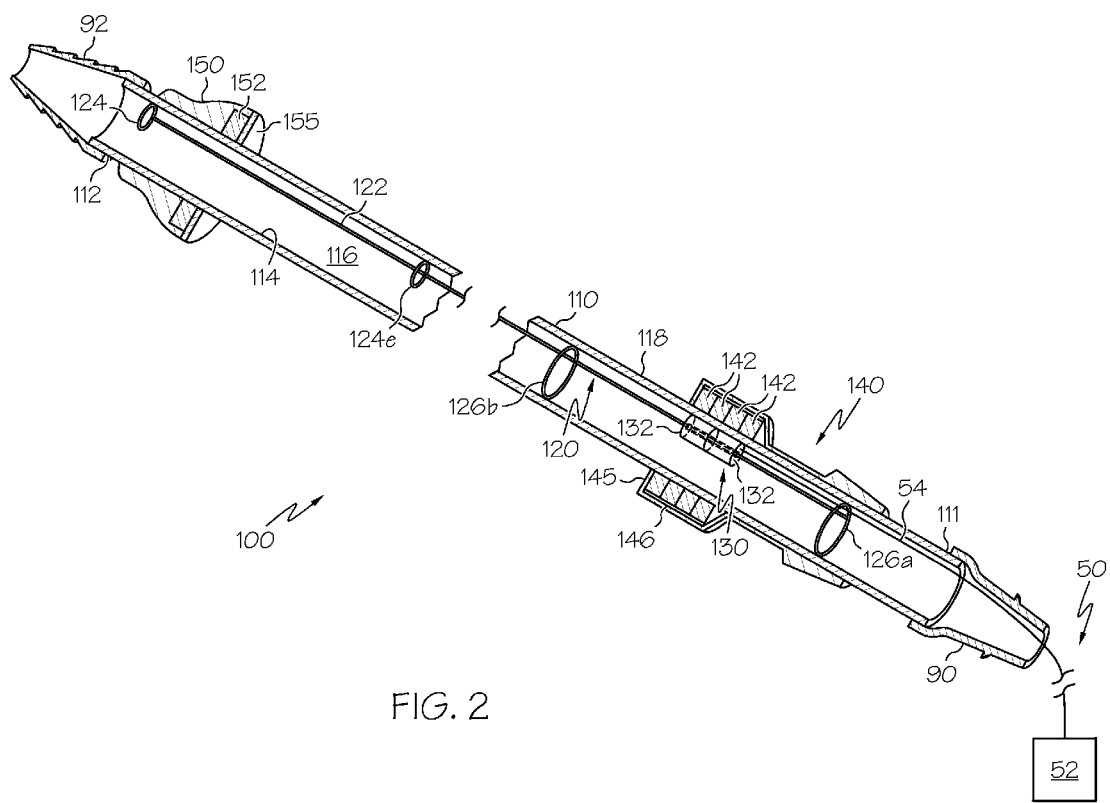
FIG. 2 is a perspective view, partially in section, of a clearance device according to an embodiment hereafter described.

Exemplary embodiments of the clearance device 100 will now be more fully described. As seen in FIG. 2, the clearance device 100 includes the shuttle guide tube 110 mentioned above. The shuttle guide tube 110 has a proximal end 111 and a distal end 112. In use, the proximal end 111 of the shuttle guide tube 110 is adapted to be connected to a suction source preferably via a suction fitting 90 secured to its proximal end, and the distal end 112 is adapted to be connected to a medical tube, such as chest tube 10, preferably via a chest-tube fitting 92 secured to its distal end. Guide tube 110 has a wall having an inner diameter 114 defining a guide-tube passageway 116 and an outer circumference 118. A shuttle member 140 is disposed over, preferably in contact with, the wall of the guide tube 110 at its outer circumference 118 and is adapted to translate along the length of the tube 110 to advance and withdraw the clearance member 124 as described below.

A wire clearance assembly 120 is at least partially disposed within the guide-tube passageway 116. The wire clearance assembly 120 includes an elongate guide member 122 and a clearance member 124 disposed in and secured to the distal region of the guide member 122, preferably at its distal end. In one embodiment, the guide member 122 can be in the form of a guide wire, and the clearance member 124 can be formed by the guide wire. For example, the terminal end of the guide wire can be wound to form a loop 124a at its terminal end. The remainder of this description is provided with reference to a guide wire as a preferred embodiment of the guide member 122. However, other embodiments of a guide member 122 are possible and will be readily ascertained by those having ordinary skill in the art; for example, an elongate flat metal or plastic strip, or other elongate form, that is flexible but biased to a straight configuration but capable to negotiate bends in the guide and medical tubes 110,10 may be used.

Figure 2A:
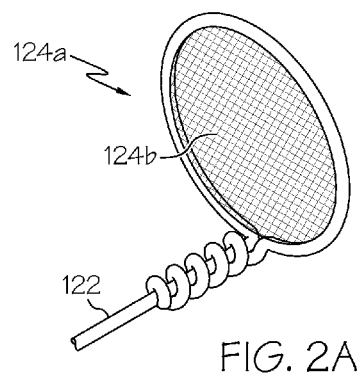
FIGS. 2a-2d illustrate various embodiments of a clearance member disposed at the distal end of a guide wire, as well as an embodiment of the guide wire having a core-and-sheath construction (FIG. 2d).

FIG. 2a illustrates one embodiment using a guide wire 122, where the terminal portion of the guide wire 122 is wound to form loop 124a, with a small amount of slack after forming the loop 124a being wound tightly along the length of the wire 122 immediately proximal to the loop 124a. The amount of slack to be so wound can be, e.g., about or less than the diameter of the loop 124a, or about or less than twice that diameter. When so wound, the slack is preferably wound so that adjacent turnings of the slack over the guide wire 122 are immediately adjacent (preferably in contact with) one another, and substantially fully in contact with the portion of the wire 122 over which they are wound.

Figure 2B:
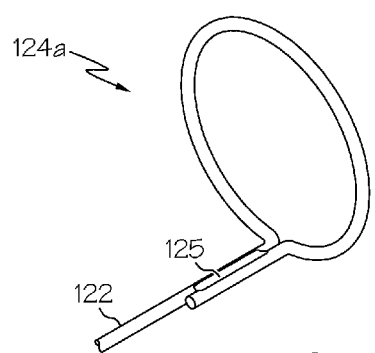
Figure 2C:
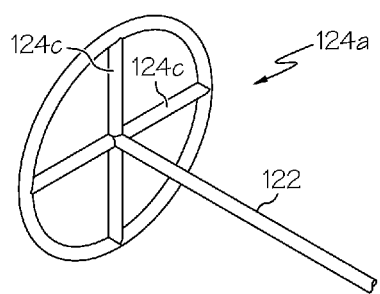
Figure 2D:
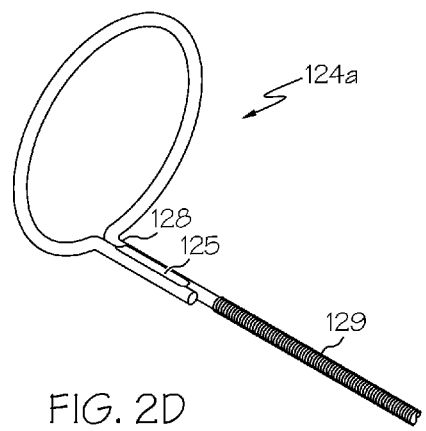

In another embodiment illustrated in FIG. 2b, the slack in the wire 122 after forming loop 124a can be soldered to the portion of the wire 122 immediately proximal to the loop 124a at solder joint 125. The slack can be positioned parallel to the portion of the guide wire 122 to which it is to be soldered, as shown in FIG. 2b. Alternatively, it may be wound around the guide wire 122 and then soldered. The length of the slack can be similar as described above with respect to FIG. 2a. Alternatively, if the slack is to be soldered in parallel to the wire 122 as seen in FIG. 2b, it is preferable that its length be about or less than one radius (½ the diameter) of the loop 124a. The diameter of loop 124a is preferably selected to substantially correspond to the diameter of the inner wall of the chest tube 10 to which the clearance device 100 will be fitted, as described in more detail below. Optionally, though perhaps less preferred, a mesh 124b (seen schematically in FIG. 2a) can be provided extending across the diameter of the loop 124a, having openings dimensioned to permit fluid to flow therethrough. In this embodiment, liquid-phase blood and other fluids will be permitted to pass through the mesh 124b from the body cavity, into the chest-tube passageway 16. Thereafter, should such blood or other fluid form a clot in that passageway 16, the mesh can assist to draw the clot out of the passageway 16 upon withdrawal of the loop 124a proximally, as described in more detail below. As noted previously in this paragraph, the guide wire 122 can be attached at the perimeter of the loop 124a, and can be formed integrally with the loop 124a. Alternatively, the guide wire 122 can be attached at the center of the loop 124a via cross members 124c as seen in FIG. 2c. However, embodiments that include elements that obstruct the opening at the center of the loop 124a (e.g. mesh 124b or cross members 124c) are less preferred due to the potential to promote obstruction of the loop 124a, e.g., by the formation of clot material attached to such elements.

As seen throughout the figures, the loop 124a lies in a plane that is at a predetermined angle, for example 90°, to the longitudinal axis of the guide wire 122 at the point where the loop 124a and guide wire 122 (e.g. the longitudinal expanse of the guide wire 122 if that wire is used to form the loop 124a) intersect. The precise angle may be subject to some variance, for example due to flexure of the guide wire 122 and loop 124a as they are advanced and/or drawn through the chest tube (explained below). Preferably the angle between the loop 124a and guide wire 122 is in the range of 75° to 105°, more preferably 80° to 100°, more preferably 85° to 95°.

The guide wire 122 can be made from conventional materials including plastics and metals. It is preferred that the guide wire 122 be made from a material having sufficient flexibility that it can reversibly bend to a radius of curvature of four centimeters, more preferably three centimeters, more preferably two centimeters or one centimeter, without snapping or substantially compromising its structural integrity. Suitable materials include nitinol, stainless steel and titanium-nickel alloys. In addition to being sufficiently flexible to negotiate bends in the chest tube 10 (or guide tube 110) on being advanced/retracted therethrough, the guide wire 122 should have sufficient stiffness or rigidity to be pushed through accumulated clot material within either tube without kinking or being caused to double back on itself.

The requisite flexibility to negotiate bends simultaneous with the requisite stiffness to be pushed through clot material may be achieved by biasing the flexible guide wire 122 to a generally straight (linear) configuration. This can be achieved, for example, utilizing a core-and-sheath construction as illustrated in close-up view in FIG. 2c. In this figure, the guide wire 122 includes a core wire 128 and a sheath wire having a smaller diameter than the core wire 128 wound around the core wire 128 to provide a spiral-wound wire sheath 129. The wire sheath 129 can be made from any suitable material, e.g., including the same or similar materials useful for the core wire, noted above.

The wire sheath 129 will tend to bias the guide wire 122 (including core wire 128 and sheath 129) into a straight or linear configuration, while still permitting the wire 122 to bend in order to traverse bends in the chest tube 10 when in use. In this embodiment, the guide wire 122 (including core wire 128 and sheath 129) still preferably can be bent to the radii of curvature noted above without snapping or substantially compromising its structural integrity. In a preferred embodiment, the sheath 129 stops short of the distal end of the guide wire 122, where the core wire 128 emerges unsheathed and is formed into the loop 124a at its distal end. In the embodiment shown in FIG. 2c, the slack in the core wire 128 after forming loop 124a is soldered to the portion of the core wire 128 immediately proximal to the loop 124a at solder joint 125, similar as in the embodiment described above with respect to FIG. 2b. However, other modes of forming and securing the loop 124a from the terminal or distal portion of the core wire 128 may be employed. In one embodiment, not shown, the loop 124a may be formed from the complete core-and-sheath construction of guide wire 122, wherein the sheath 129 continues around the loop 124a. Alternatively, a separate clearance member 124 may be secured at or in the vicinity of the distal end of the guide wire 122, whether a sheath 129 is employed or not.

Optionally, whether a sheath 129 is employed or not, the guide wire 122 may be coated substantially along its length with a friction-reducing material, to help prevent agglomeration of debris (such as blood clots) to the guide wire, and also to assist in transitioning the guide wire around bends in a chest tube 10 where it is to be inserted. Suitable coating materials for this purpose include, e.g., Teflon (polytetrafluoroethylene) compositions, polyurethane compositions, other hydrophilic polymers, and other coatings, including coatings comprising therapeutic agents such as a heparin coating or antibiotic coating.

Still referring to FIG. 2, a magnetic guide 130 is secured to the guide wire 122 in the proximal region thereof. The magnetic guide 130 can comprise one or a plurality of first or inner magnetic elements 132. The first magnetic elements 132 can be permanent magnets. Alternatively, they can be metal elements having magnetic properties, which are not necessarily permanent magnets. As used herein, a metal element has magnetic properties if it is capable of being attracted by a permanent magnet via magnetic forces. The magnetic guide 130 can be secured to the guide wire 122 via any suitable or conventional means. FIG. 3a illustrates an exploded view of an exemplary embodiment of the magnetic guide 130. In this embodiment, a plurality (two are illustrated) of cylindrically-shaped permanent magnets 132a having axial through bores are coaxially aligned adjacent one another, with washer 133 disposed therebetween. The magnets 132a are oriented such that their respective North and South poles face the same direction. This results in the two magnets attracting one another at their adjacent faces. In practice, this results in the magnets 132a attracting one another so that both contact the intermediate washer 133, and sandwich and retain that washer between them. The guide wire 122, extending from its distal end, passes through the axial bore of at least the distal-most magnet 132a and is secured to the washer 133, e.g. by welding or braising. Alternatively, the guide wire 122 can be secured to the washer 133 by wrapping it one or more times through the washer bore as illustrated in FIG. 3b.

Figure 3C:
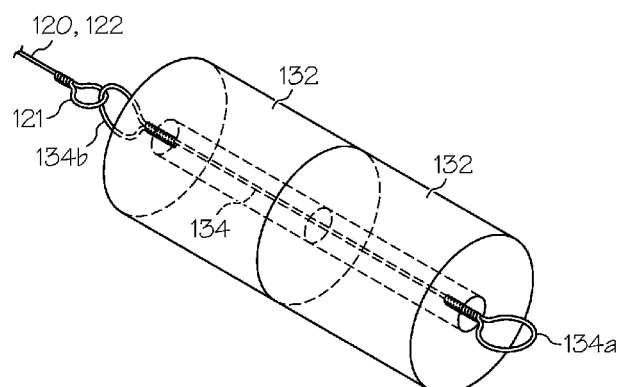

In still a further embodiment shown in FIG. 3c, a retention wire 134 can be fed through the axial bore(s) of one or more first magnetic element(s) 132. Portions of the retention wire 134 emerging from opposite ends of the element(s) 132 are wound into retentive wire loops 134a,134b whose diameters are larger than the through bore(s) of the element(s) 132. The guide wire 122 then can be secured to the distal retentive wire loop 134b via a proximal loop 121 thereof, which interlocks the retentive wire loop 134b. In this embodiment, the element (s) 132 may or may not be permanent magnets. Optionally, the guide wire 122 may continue through the axial bore of the proximal-most magnet 132a at least some distance as illustrated.

Figure 3D:
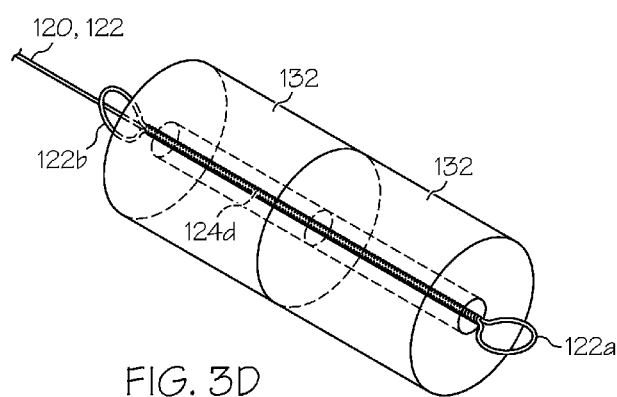

In still a further embodiment, the guide wire 122 itself can form a retentive portion 124d thereof that retains the first magnetic element(s) 132 in place secured in the proximal region thereof. In one such embodiment illustrated in FIG. 3d, the guide wire is fed through the axial bore(s) of the first magnetic element(s) 132 in a proximal region of the wire 122. A portion of the guide wire emerging from the proximal end of the element(s) 132 is wound into a first guide wire retentive loop 122a. The guide wire 122 is separately wound into a second guide wire retentive loop 122b where it emerges from the distal end of the element(s) 132, before proceeding toward the guide wire distal end. The guide wire retentive loops 122a,122b fix the first magnetic element(s) 132 in position and secure it relative to the guide wire 122 in a proximal region thereof.

The foregoing are but a few ways in which the first magnetic element(s) 132 can be secured to the guide wire 122 in its proximal region. Numerous other modes of securement are possible, and will be readily discernible and implemented by the person having ordinary skill in the art. For example, there will be apparent to the person having ordinary skill in the art numerous additional ways to use loops, solder or braising joints, wire knots, and combinations of these, either in the guide wire 122 itself or in a separate retention wire 134, with or without washers or other similar elements, to secure the first magnetic elements 132 to one another, and to secure all of them in place and attached to the proximal end or in the proximal region of the guide wire 122. In still a further alternative, the guide wire may be soldered or braised directly to one or more first magnetic element(s) 132, with or without axial bores therein. As will also be appreciated, where two such magnetic elements 132 are used, it is not necessary that both are permanent magnets or that both are not permanent magnets. The first magnetic elements 132 may optionally be present as one (or more) of each. However, in embodiments where retentive forces between them may be relied upon to hold them in place relative to the guide wire 122, such as the embodiments illustrated in FIGS. 3a and 3b, using two permanent magnets as the elements 132 should produce a stronger attractive force between them, resulting in more securely retaining them to the guide wire 122.

Figure 4:
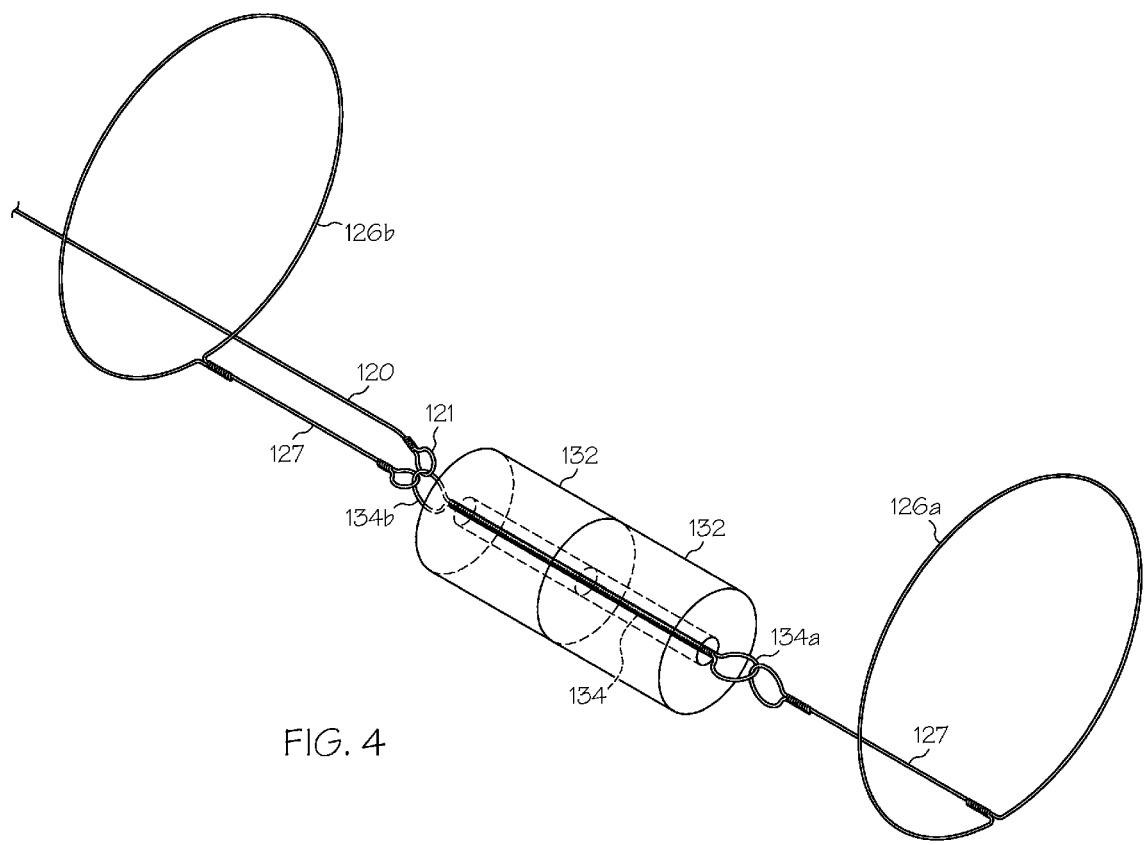
FIG. 4 illustrates a magnetic guide according to a disclosed embodiment, having retaining members attached at either end to retain the proximal region of the guide wire within the guide tube.

Referring now to FIGS. 2 and 4, the wire clearance assembly 120 preferably also includes proximal and distal retaining members 126a and 126b secured to the respective ends of the first magnetic element(s) 132. The retaining members 126a, 126b are dimensioned so that they cannot pass through either the proximal or distal end, respectively, of the guide tube 110, thereby retaining the first magnetic element(s) 132 and the associated proximal region of the guide wire 122 inside the tube 110, within the guide tube passageway 116. For example, the retaining members 126a,126b can be provided in the form of wire loops having diameters substantially corresponding to that of the inner diameter 114 of the shuttle guide tube 110, which will thereby be prevented from passing through the fittings at either end of the tube 110, both of which preferably have smaller-diameter clearances compared to the guide tube 110. Preferably, both the chest tube 10 and the vacuum tube 210 (if present) also have smaller inner-wall diameters than the shuttle guide tube 110, thereby further preventing either retaining member 126a,126b from exiting the guide tube 110 to enter the respective chest or vacuum tube. When provided in the form of wire loops, the retaining members 126a,126b can be made from lengths of wire that are retained to the first magnetic element(s) 132 in any suitable or conventional manner. For example, as seen in FIG. 4, each retaining member 126a,126b can be secured via a wire loop that interlocks with the respective guide wire retentive loop 122a,122b or retentive wire loop 134a,134b disposed at either end of the first magnetic element(s) 132. In the illustrated embodiment, retaining members 126a,126b are large wire loops having diameters substantially corresponding to the inner diameter 114, wherein tail sections 127 of each member 126a,126b extend toward and terminate in a small loop that interlocks with the adjacent retentive wire loop 134a,134b.

Figure 5:
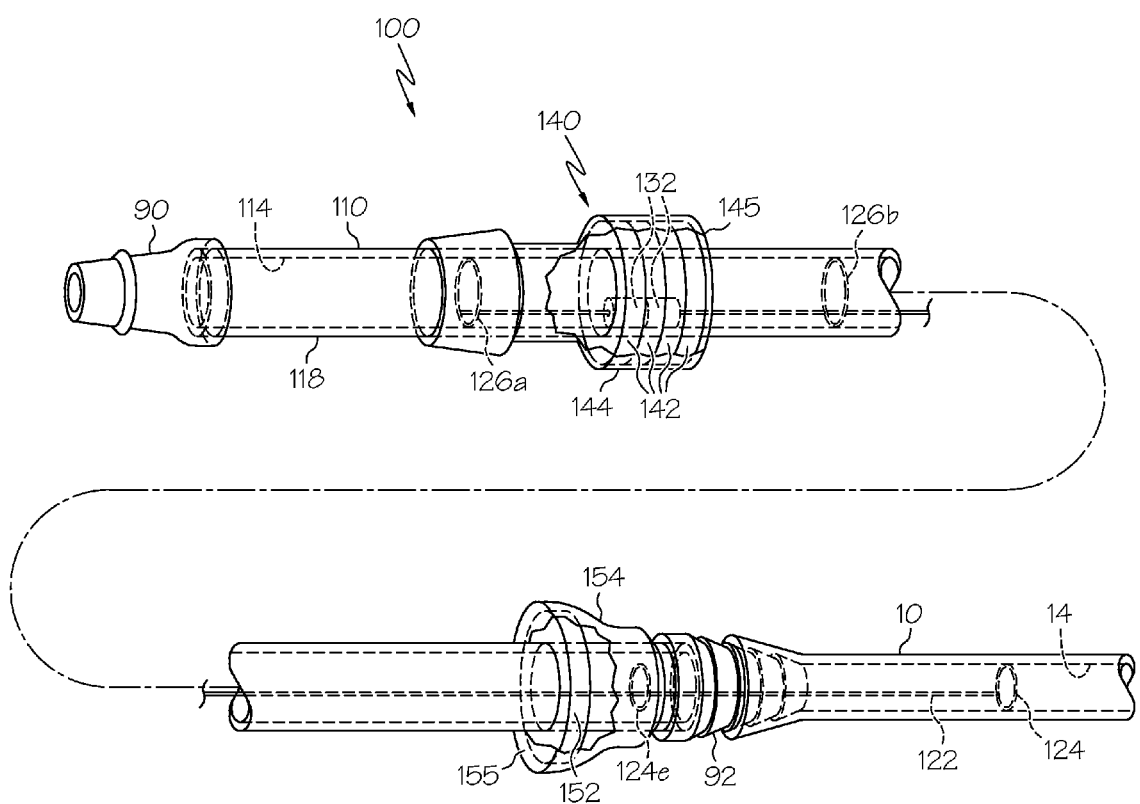
FIG. 5 is a perspective view, partially in section, of an embodiment of a clearance device as hereafter described and including one embodiment of a shuttle member and shuttle stop on the outside of the guide tube. The guide tube is coupled to a chest tube to facilitate clearing obstructions therefrom.

As noted above and most clearly seen in FIGS. 2 and 5, shuttle member 140 is disposed over, preferably in contact with, the outer circumference 118 of the guide tube 110. The shuttle member 140 has a through bore preferably having a diameter substantially corresponding to the outer circumference 118, such that the shuttle member 140 can slidably and smoothly translate along the length of the guide tube 110 with the guide tube 110 received through its bore. The shuttle member 140 includes one or a plurality of second or outer magnetic elements 142 embedded or enclosed within a shuttle housing 144. Optionally, the second magnetic element(s) 142 can form all or part of the housing 144. Alternatively, the shuttle member 140 may consist only of the second magnetic element(s) 142. In the illustrated embodiment, the second magnetic elements 142 are provided in the form of rings wherein the guide tube 110 passes through openings at the center of each said ring. As with the first magnetic elements 132 discussed above, the second magnetic elements can be permanent magnets or, alternatively, metal elements having magnetic properties that are not necessarily permanent magnets. However, for reasons that will become clear either at least one of the first magnetic elements 132 or at least one of the second magnetic elements 142 should be a permanent magnet. In preferred embodiments, both the first and second magnetic elements 132 and 142 are permanent magnets. Optionally, a magnetic shield 146 can be provided surrounding or substantially surrounding the second magnetic elements 142, either within the shuttle housing 144 or as part of or forming that housing. The magnetic shield 146 should not be disposed between the first and second magnetic element(s) 132,142, however. Depending on the magnetic strength of the second magnetic elements 142, such a shield 146 may be desirable in circumstances where a strong magnetic field may interfere with medical equipment to be located in close proximity with the clearance device 100, for example an implanted pace maker. While the shield 146 cannot completely enclose the magnetic elements 142 (e.g. the tube 110 preferably passes through the shuttle member 140 and the first and second magnetic element(s) 132,142 must be able to magnetically interact with one another), it will help to reduce the magnetic field that extends beyond the shuttle member 140.

As will be appreciated, it may be impractical to provide a similar shield around the first magnetic elements 132 because they need to be free to magnetically interact with the second magnetic elements 142. However, in the embodiment shown in FIG. 2, when the first and second magnetic elements 132, 142 are magnetically coupled, all such magnetic elements 132,142 will be disposed within the volume of the shuttle housing 144, and consequently within the magnetic shield 146. In further embodiments, the first magnetic elements 132 may be provided as metal elements that are not permanent magnets, or as relatively weak permanent magnets, so as not to create strong magnetic fields that may interfere with other equipment in the event they become decoupled from the second magnetic elements 142.

When provided as permanent magnets, preferably both the first and second magnetic elements 132 and 142 have axially-aligned North-South polarity relative to the longitudinal axis of the guide tube 110. Less preferably, magnetic elements 132 and 142 having radially-aligned North-South polarity can be used. These are less preferred, however, due to the increased attraction between them through the guide-tube wall, which results in increased friction when translating the shuttle member 140 along the tube 110 length to advance or withdraw the clearance member 124 (explained below). Conversely, it has been found that magnets having axially-aligned polarity can provide suitable attractive force between the magnetic elements 132 and 142 to retain the magnetic guide 130 and shuttle member 140 in tandem while translating the shuttle member 140 along the tube 110 length, without unduly increasing friction as they translate along the tube 110. For example, neodymium magnets (N5-N50) may be used as permanent magnets herein. Neodymium magnets generally are the strongest permanent magnets, so it may not be desirable to use such magnets as both the first and the second magnetic elements 132 and 142, otherwise undue friction against the tube 110 may result. The selection of particular magnets, having appropriate magnetic strength, is well within the capability of a person having ordinary skill in the art. In preferred embodiments, the magnetic elements 132 and 142, and their cooperative attractive strengths, are selected to allow a high degree of attractive force to prevent as much as possible instances of magnetic de-coupling between the wire guide 130 and the shuttle member 140, while at the same time minimizing their weight and bulk.

A shuttle stop 150 is secured to the outer circumference 118 of the guide tube 110 in a distal region thereof, preferably just proximal to the distal end of the guide tube 110. The shuttle member 140 and shuttle stop 150 preferably have complementary first and second parking surfaces 145 and 155, which face one another. As the shuttle member 140 is translated distally along the length of the guide tube 110, it approaches and ultimately reaches a parking station wherein the respective parking surfaces 145 and 155 are in contact or disposed adjacent one another. The shuttle stop 150 has a parking magnetic element 152 enclosed or embedded within a shuttle stop housing 154, just behind or forming the second parking surface 155. The parking magnetic element 152 can be made from similar or the same materials as the first and second magnetic elements 132 and 142 discussed above, except that at least the parking magnetic element 152 or second (outer) magnetic element 142 should be a permanent magnet. In this manner, the outer magnetic element 142 and parking magnetic element 152 will attract one another when the shuttle member 140 is parked against the shuttle stop 150, thus retaining the shuttle in the parked position when not being actively used to actuate the clearance member 124. In this embodiment, if present the magnetic shield 146 should not extend between the second magnetic element 142 and the parking magnetic element 152.

Figure 6:
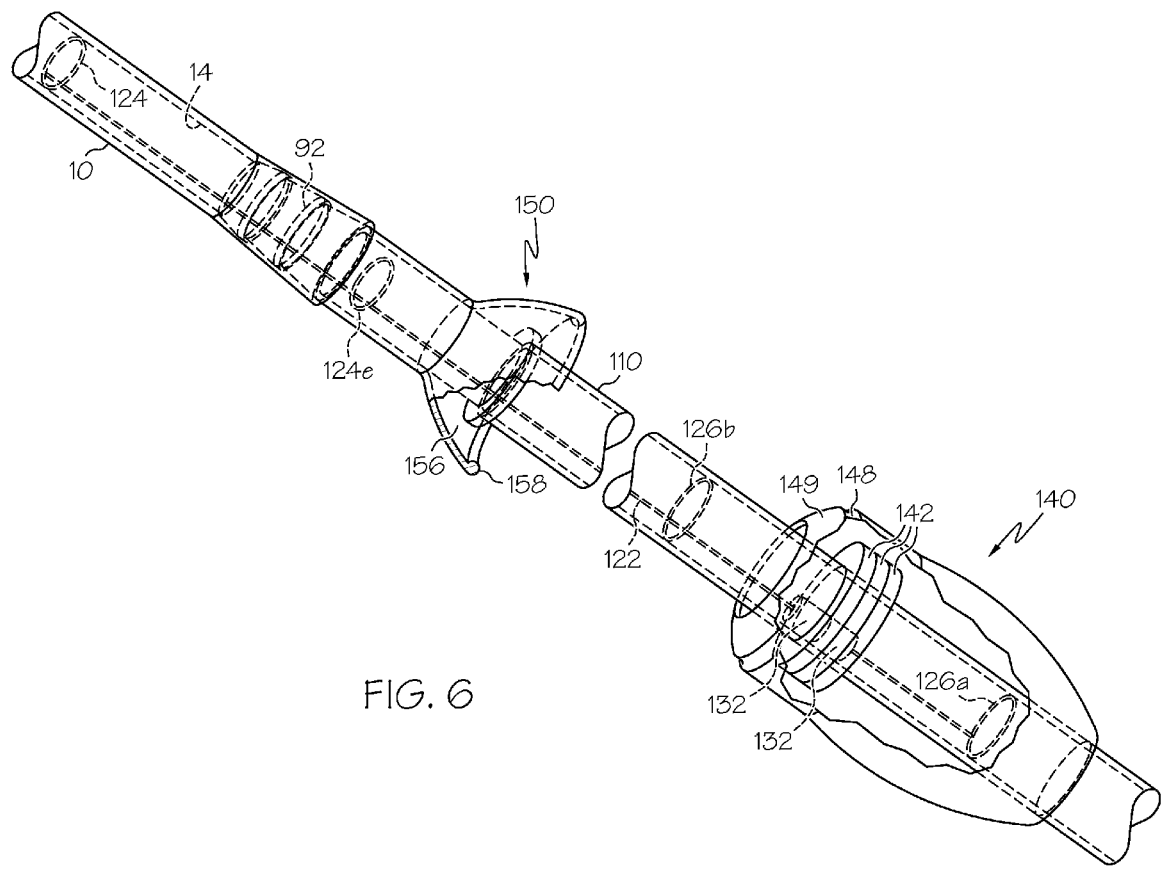
FIG. 6 is a perspective view, partially in section, of an embodiment of a clearance device as hereafter described and including a further embodiment of a shuttle member and shuttle stop.

Alternatively, the shuttle member 140 can be retained in the parked position against the shuttle stop 150 via a reversible mechanical attachment mechanism. For example, FIG. 6 shows an embodiment employing a click-and-park mechanism between the shuttle member 140 and the shuttle stop 150. In this embodiment, the shuttle stop 150 defines a shuttle socket 156 to receive the distal portion of the shuttle member 140 therein. The shuttle socket 156 includes a parking rib or flange 158 disposed around the circumference of the socket 156 wall and extending radially inward. The shuttle member 140 has a complementary parking groove 148 disposed in the exterior circumference of the shuttle housing 144, and an annular camming surface 149 disposed at or forming the distal end of the housing 144. The groove 148 is preferably disposed immediately behind the camming surface 149. As the shuttle member 140 advances and is seated within the socket 156, the flange 158 initially engages the camming surface 149, which radially expands the flange 158 as the shuttle member 140 is advanced, until the flange 158 is received and accommodated within the groove 148, beyond the camming surface.

While magnetic and mechanical flange-and-groove locking mechanisms have been described here, it will be appreciated that any suitable or conventional mechanism to reversibly lock and retain the shuttle member 140 in the parked position adjacent or in contact with the shuttle stop 150 could be employed.

Figure 7:
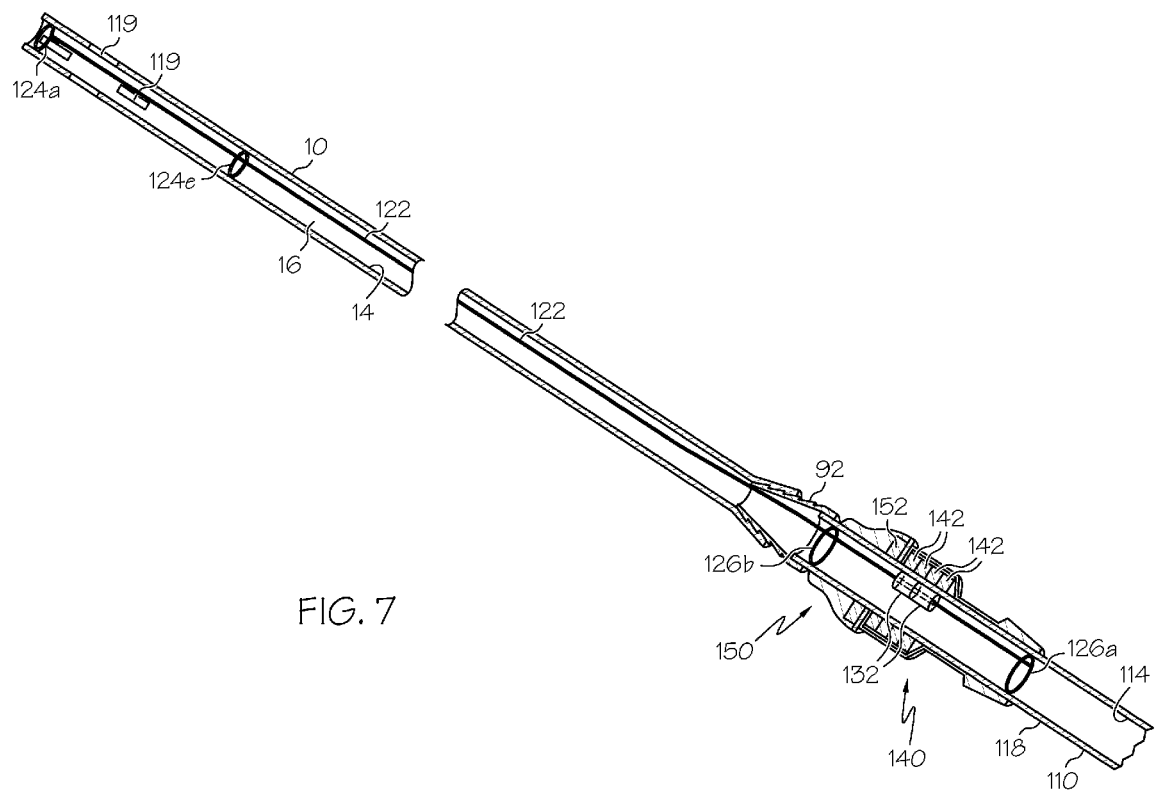
FIG. 7 is a perspective view of a clearance device coupled to a chest tube, according to an embodiment hereafter described.

Referring now to FIG. 7, the clearance device 100 described above is shown fitted to a chest tube 10. The chest tube 10 has a wall having an outer circumference 18 and an inner diameter 14 that defines a chest-tube passageway 16. In desirable embodiments, the diameter of the chest-tube passageway 16 (diameter 14) is smaller than that of the guide-tube passageway 116 (diameter 114). The distal end of the clearance device 100 (shuttle guide tube 110) is fitted to the proximal end of the chest tube 10 via chest-tube fitting 92. The chest-tube fitting 92 preferably ensures a fluid-tight connection between the distal end of the shuttle guide tube 110 and the proximal end of the chest tube 10, while providing fluid communication between the chest-tube passageway 16 and the guide-tube passageway 116. For this purpose, a conventional barbed reducer fitting can be used, as illustrated for the fitting 92 in the drawings. To achieve a fluid-tight fitment, proximal end of the chest tube 10 is forcibly fitted over the barbs provided at the outer surface of the fitting 92, so that the barbs enter the chest-tube passageway 16 just at its proximal end to engage its inner diameter 14 in a conventional manner. Preferably, the chest tube 10 is made from a material having elastic properties, such as silicone, which will help ensure a fluid-tight seal because the tube 10 will tend to contract over the barbs of fitting 92. A flexible, elastic tube 10, e.g. made from silicone, also will result in reduced discomfort for the patient compared to more rigid chest-tube materials, such as polypropylene or polyethylene However, if desired these and other rigid materials may be used. Other elastic materials, including elastic thermoplastics, also may be used in place of silicone, if desired. Preferably, the chest tube 10 is made from a clear (i.e. transparent or substantially transparent) plastic material, so the operator of the clearance device 100 described herein can visualize any clot material or other debris therein, as well as its removal as described below.

With the clearance device 100 and chest tube 10 fitted together as described above, the guide wire 122, and the clearance member 124 disposed at its distal end, may be advanced into and withdrawn from the chest tube 10 to assist in clearing debris therefrom as follows. In use, the magnetic guide 130 and shuttle member 140 are magnetically attracted to one another by means of the cooperating magnetic elements 132 and 142. This results in coupling the magnetic guide 130 to the shuttle member 140 via magnetic forces that act through the wall of the shuttle guide tube 110. Consequently, sliding or translating the shuttle member 140 along the length of the shuttle guide tube 110 induces a corresponding translational movement of the magnetic guide 130 magnetically coupled thereto, and of the guide wire 122 that is secured to the magnetic guide 130. In FIG. 7, the shuttle member 140 is illustrated in the parked position, in contact with the shuttle stop 150. The length of the guide wire 122 between its distal end and the point where it is secured to the wire guide 130 is preferably selected to substantially equal to the length of the chest tube 10 plus the length corresponding to the distance between the shuttle stop 150 and the point where the chest tube 10 engages the fitting 92. In this embodiment, when the shuttle member 140 is parked against the shuttle stop 150 (having the wire guide 130 in tandem therewith along the guide-tube 110 length), the clearance member 124 at the distal end of the guide wire 122 is disposed within the chest tube 10 adjacent its distal end and does not emerge from the chest tube 10 into the body cavity. In a preferred embodiment, this is the parked position of the clearance member 124, where it normally rests when the device 100 is not being used to actively remove debris from the chest tube 10. As seen in FIG. 7, the chest tube 10 can have one or a plurality of apertures 119 through the wall of the tube 10 in the distal region thereof, to assist in suctioning and drawing fluid located in the body cavity where the chest tube 10 is placed. Preferably, the clearance member 124 is dimensioned and oriented so that it cannot pass through the apertures 119, to emerge laterally from the chest tube 10. In the illustrated embodiment, the diameter of the wire loop 124a is too large to fit through the width of apertures 119 based on its orientation, which is fixed relative to the guide wire 122. In addition, it may be desired that the length of apertures 119 also be smaller than the loop 124a diameter.

In operation, with the chest tube 10 (its distal end) inserted in a body cavity of a patient and the shuttle guide tube 110 being connected to a suction source 200 at its proximal end, fluid from the body cavity is drawn into and through the chest-tube passageway 16, then through the guide-tube passageway 116 to be collected or disposed of in any suitable or conventional manner, such as in a conventional collection canister (not shown). In the illustrated embodiment, the clearance member 124 is in the form of a wire loop 124a. The diameter of the wire loop 124a preferably substantially corresponds to the diameter of the inner diameter 14 of the chest tube 10, such that the loop 124a scrapes the inner diameter 14 as it translates along the chest-tube 10 length. The diameter of the wire itself that forms the wire loop 124a is very small, preferably about or less than 10%, preferably 8%, preferably 6%, preferably 5% or 4%, the diameter of the inner diameter 14, to provide a substantially unobstructed pathway from the distal end of the chest tube 10 into and through its passageway 16, through the loop 124a. Fluid and other debris drained from the body cavity pass into the chest-tube passageway 16, through the loop 124a, and proceed proximally toward the suction source 200. As such fluid moves through the chest tube passageway 16, particularly fluids comprising blood or platelets, the fluid can form or produce clots that stick to the inner diameter 14 of the chest tube 10. As the clots form or build, they begin to obstruct the chest-tube passageway 16, inhibiting drainage. If left unchecked, such clots may completely obstruct the passageway 16, rendering the chest tube 10 inoperative.

Figure 8A:
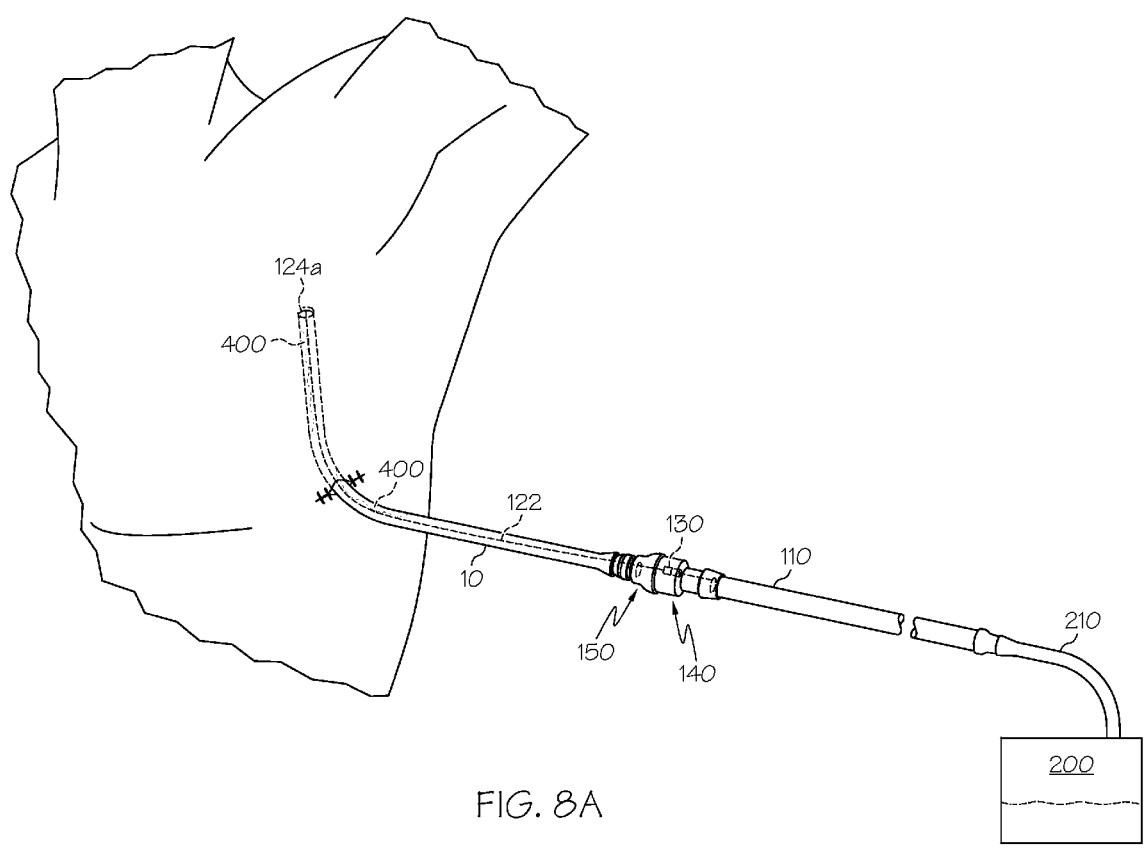
FIGS. 8a-8c are similar views as in FIG. 7, but showing the shuttle member, and correspondingly the guide wire and clearance member, at different stages of advancement for clearing obstructions from the chest tube.
Figure 8B:
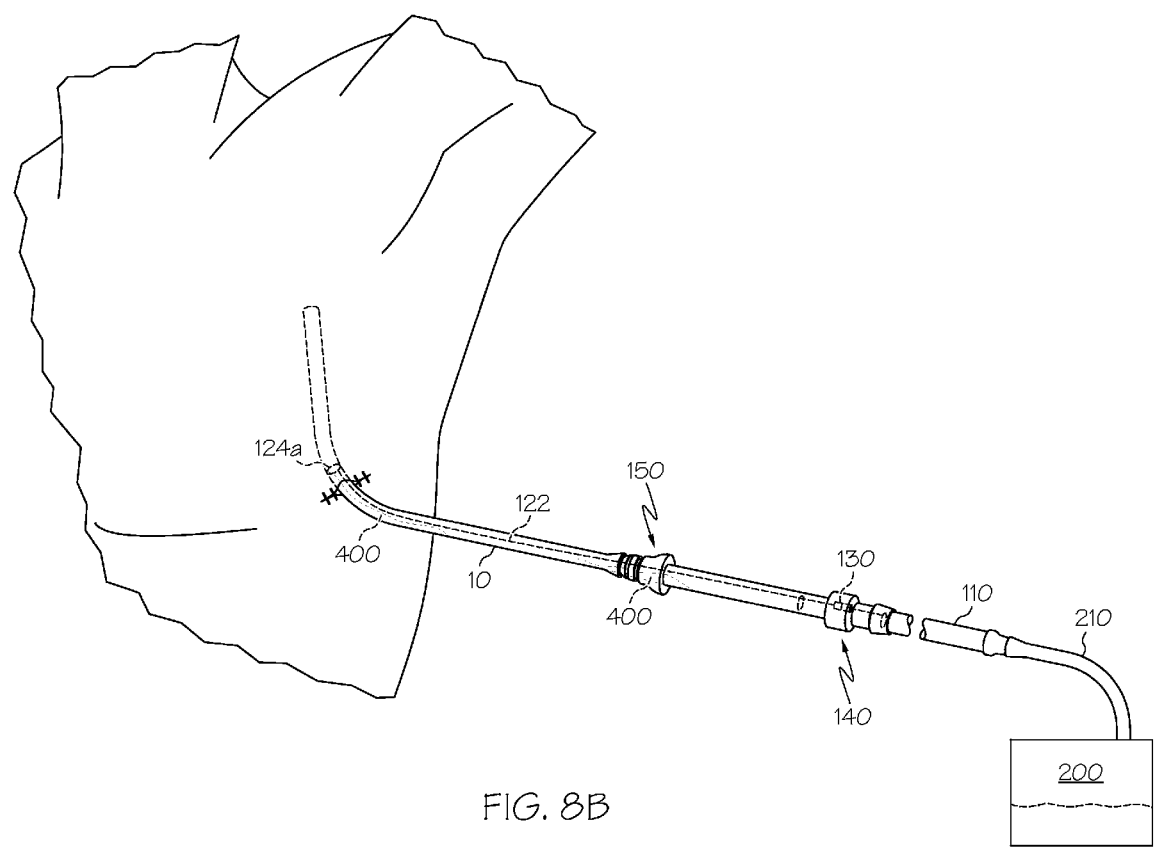
Figure 8C:
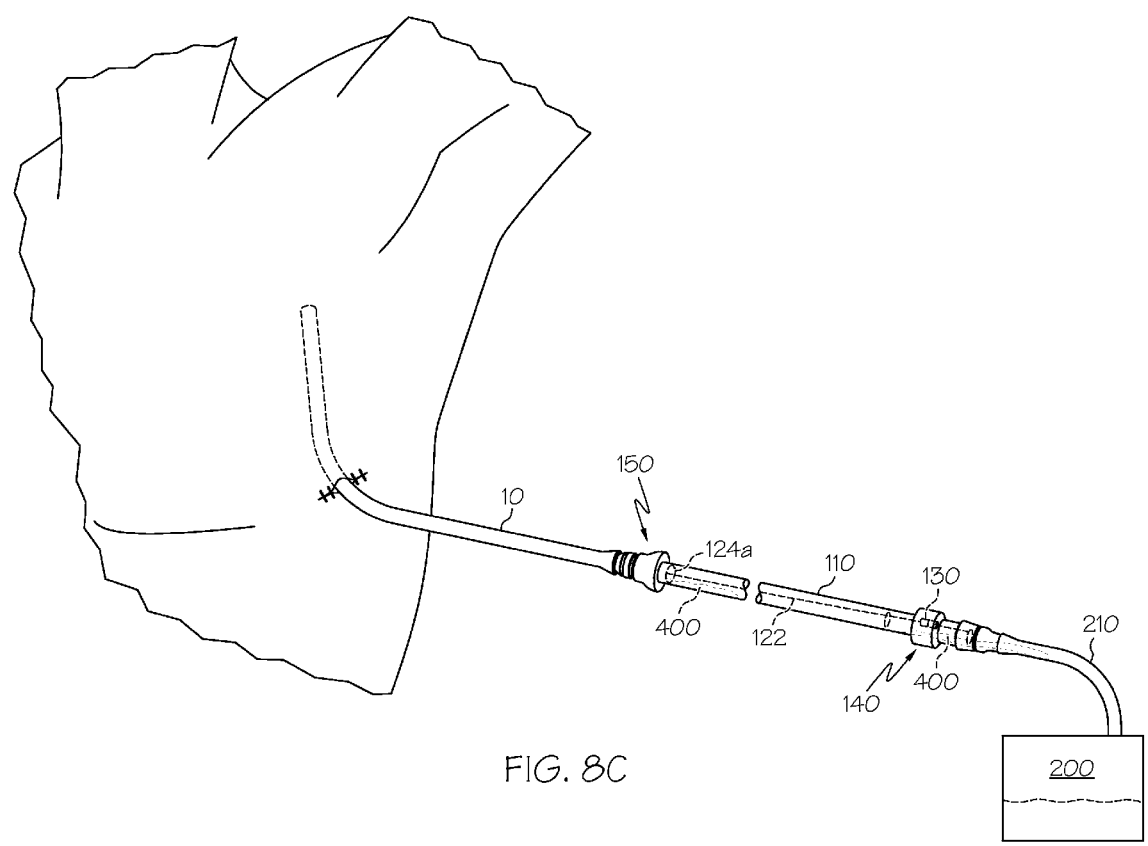

As noted above, the clearance member 124 (e.g. loop 124a) is normally disposed adjacent the distal end of the chest tube 10 inside the chest-tube passageway 16. This position of the clearance member 124 corresponds to the shuttle member 140 being in the parked position adjacent or in contact with the shuttle stop 150, as seen in FIG. 8a. To help clear the chest tube 10 of clots and other debris 400 accumulated therein, a nurse, physician or other operator grasps the shuttle member 140 and pulls it proximally along the length of the guide tube 110, toward the tube's 110 proximal end. The attractive magnetic force between the first and second magnetic elements 132 and 142 retains the magnetic guide 130 in tandem with the shuttle member 140 as the latter translates proximally, which in turn draws the guide wire 122 and clearance member 124 proximally through the chest-tube passageway 16 as seen in FIG. 8b. As the clearance member 124 is drawn proximally, it engages clot material and other debris in its path and forces such material and debris proximally (FIGS. 8b, 8c), toward the proximal end of the chest-tube passageway 16 and ultimately out of that passageway, and into the guide-tube passageway 116 (FIG. 8c). To carry out this operation, preferably the operator grasps the shuttle member 140 with one hand and the proximal end of the guide tube 110 with the other hand so that the pulling force applied to the shuttle member 140 is applied against a counter-force applied to the tube 110 via the other hand, and not against the sutures retaining the chest tube 10 in place in the patient. Alternatively, the same objective can be achieved by grasping a different portion of the guide tube 110, or the shuttle stop 150, with the other hand before sliding the shuttle member 140. Optionally, the clearance member can be alternately withdrawn and advanced from/into the chest-tube passageway 16 to help break up clot material or other debris, as well as to aid in drawing such debris proximally. Once the clearance operation has ended, the shuttle member 140 may be advanced back into its parked position adjacent or in contact with the shuttle stop 150, which correspondingly will advance the clearance member 124 back into its normal resting position adjacent the distal end of the chest tube 10.

As noted above, the inner diameter 114 of the guide tube 110 preferably has a larger diameter than the inner diameter 14 of the chest tube 10. Consequently, debris removed from the chest tube 10 and into the guide tube 110 will be less obstructive in the guide tube 110, and more readily drawn out via suction applied by the suction source 200. Alternatively, a guide tube 110 that eventually becomes fully obstructed will be more readily and easily replaced than a chest tube, which is surgically implanted through the patient's body wall and would require revision surgery, and additional opportunity for injury and infection, to replace.

In the event the magnetic guide 130 becomes magnetically de-coupled from the shuttle member 140, the retaining members 126a,126b discussed above will prevent the magnetic guide 130, and the proximal portion of the guide wire 122 where it is attached, from exiting the guide tube 110. In preferred embodiments where the chest tube 10 (and vacuum tube 210 if present) have smaller inner diameters compared to the guide tube 110, the retaining members 126a,126b are dimensioned so they will not fit into either tube secured to the opposite ends of the guide tube 110. In addition, the fittings 90 and 92 secured at opposite ends of the guide tube 110 preferably are reduced-diameter fittings that have or taper to smaller inner diameters than the inner diameter of the guide tube 110 (passageway 116), which also will prevent the retaining members 126a,126b from passing therethrough. Preferably the distal retaining member 126a is positioned along the length of the guide wire 122 so as to prevent the clearance member 124 from emerging beyond the distal end of the chest tube 10 within the patient in the maximum state of advancement of the guide wire 122, with the retaining member 126a abutting either the fitting 92 or the proximal end of the chest tube 10. As will be appreciated, de-coupled magnetic guide 130 and shuttle member 140 may be magnetically re-coupled by advancing the shuttle member 140 forward until magnetic coupling therebetween is re-established, for example once the guide wire (and magnetic guide 130) are fully advanced as far as the retaining member 126a will permit. Alternatively, the operator may squeeze the chest tube 10 or guide tube 110 to manually engage the guide wire 122 through the tube wall and hold it in position while the shuttle member 140 is translated so as to magnetically re-engage the magnetic guide 130 through the guide-tube 110 wall.

In the embodiments described above, the shuttle stop 150 is disposed in the distal region of the guide tube 110, so that in the parked position of the shuttle member 140 the clearance member 124 is disposed adjacent the distal end of the chest tube 10. In this embodiment, to clear debris from the chest tube 10, the shuttle member 140, and consequently the clearance member 124, is/are drawn proximally along the guide-tube 110 length, so the clearance member 124 engages and draws debris proximally, out from the chest tube 10. In an alternative embodiment, the shuttle stop 150 can be disposed facing the opposite direction in the proximal region of the guide tube 110, so that when the shuttle member 140 is parked adjacent thereto the clearance member 124 is disposed adjacent the proximal end of the chest tube 10. In this embodiment, the shuttle member 140 is advanced distally so that the clearance members 124 enters and approaches the distal end of the chest tube 10 (chest tube passageway 14), preferably past any debris therein, before being withdrawn again proximally to draw debris out of the chest tube 10. This embodiment is less preferred, because it may result in advancing debris out of the distal end of the chest tube 10 when the clearance member 124 is first advanced therein from its resting position adjacent the proximal end of the chest tube 10.

Optionally, in addition to the clearance member 124 disposed at the distal end of the guide wire 122, there may be one or more additional clearance members 124e disposed along the length of the guide wire 122 between the distal clearance member 124 and the proximal region of the guide wire 122, to help dislodge clots and other debris along the length of the chest-tube passageway 116, for example via a back-and-forth motion of the guide wire 122.

Figure 9:
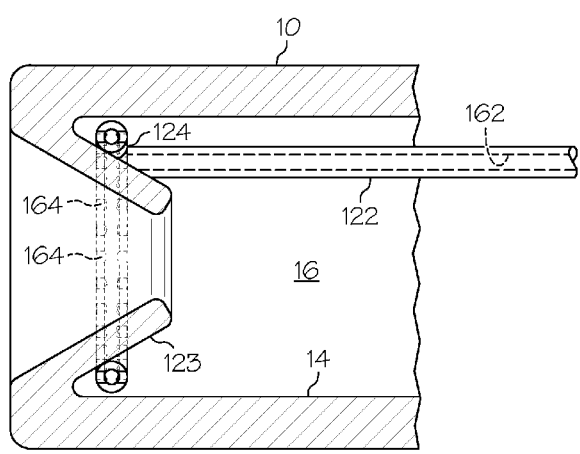
FIG. 9 is a side view, partially in section, of the distal region of a medical tube according to an embodiment hereafter described, which includes a clearance-member seat disposed at the distal end of the medical tube.

In one embodiment illustrated in FIG. 9, the chest tube 10 can include a conical clearance-member seat 123 extending radially inward and in a proximal direction from the distal end of the chest tube 10, within the chest-tube passageway 116. In this embodiment, when a clearance member in the form of loop 124a is seated at the distal end of the chest tube 10 after use, as by re-parking the shuttle member 140 at its parking station adjacent or in contact with shuttle stop 150, the seat 123 projects through the clearance-member loop 124a, thereby dislodging any clot material that may be adhered to the loop 124a. In certain embodiments, such a clearance-member seat 123 may be less preferred due to a tendency to increase the incidence of clogging the entrance to passageway 16 at the distal end of the chest tube 10.

In a further embodiment, the guide wire (or more generally guide member) 122 can have a guide lumen 162 provided in fluid communication with one or more openings 164 disposed through the wall of the loop 124a (or other clearance member 124). The guide lumen 162 and cooperating openings 164 may be utilized to deliver flushing or irrigation fluid to assist in dislodging any material stuck to the clearance member loop 124a. In addition or alternatively, fluid expelled from guide lumen 162 through openings 164 may be a solution provided to assist in the dislodgment, dissolution and/or breakup of the debris. Fluids suitable for the particular purpose include, but are not limited to, anti-thrombolytic agents, Alkalol™, among others. In still other embodiments, such fluid may be or include a therapeutic agent such as but are not limited to antibiotic agents, anti-neoplastic agents, and other agents for a variety of purposes, including pain relief, treatment of infection, cancer, or to induce scarring (i.e. pleurodesis). Fluid may be delivered into the guide lumen 162, for example, by connecting a length of flexible tubing (not shown) to the proximal end of the guide wire 122 (in communication with the lumen 162 therein), and connecting the other length of flexible tubing to a fitting 115 (shown schematically in FIG. 1) located proximally of the guide tube 110. The length of flexible tubing should be sufficient to accommodate the full range of motion in the guide wire 122 without being disconnected from either the guide wire 122 or the fitting 115, based on translating the shuttle member 140 along the full length of the guide tube 110, from adjacent its proximal end up until further advancement is prevented by the shuttle stop. The fitting 115 can have a conventional receiver on the outside to mate with a syringe or other fluid-delivery device, to communicate a fluid from the delivery device through the flexible tubing, and into and through the guide lumen 162 to emerge through openings 164. The fitting can be any conventional fitting to permit fluid communication from outside the sterile field to the flexible tubing without introducing or minimizing the introduction of contaminants therein from the outside. Positioning the fitting 115 proximal to the guide tube 110 should minimize the potential for contamination of the sterile field, so long as the suction remains active.

Alternatively to delivering fluids, the guide lumen 162 may be used to detect carbon dioxide in the chest cavity as a means to determine whether there is a puncture in a patient's lung. In this mode of operation, the proximal end of the guide lumen 162 is provided in fluid communication with a $CO_2$-sensing instrument or appropriate litmus paper that can sense the presence of $CO_2$, e.g. via a color change. This instrument/litmus paper may be provided in communication with the fitting 115 outside the sterile field. Alternatively to sensing $CO_2$ through the guide lumen 162, it may be more desirable to instead provide $CO_2$-sensing equipment in communication with the main chest-tube lumen (inner diameter 14), to sense the presence of $CO_2$ in the chest tube. This can be achieved, for example, by placing a $CO_2$-sensor, such as a sensing transducer or a holder for $CO_2$-sensitive litmus paper, in-line between the chest tube 10 and the suction source 200, for example between the guide tube 110 and suction tube 210 at the location of fitting 115 shown in FIG. 1. In this embodiment, $CO_2$ passing from the chest tube 10 to the suction source will pass through the $CO_2$ sensor, permitting the sensor to alarm if $CO_2$ is detected. In a further alternative, the $CO_2$ sensor may be coupled to the chest tube lumen via a lateral channel 330, described below (see FIG. 12).

As mentioned previously, it is conventional to select relatively large-diameter chest tubes 10, or to place more than one tube, to provide excess drainage capacity as a hedge against the formation of clots, which may obstruct drainage. A common size for a conventional chest tube 10 is 32-French. When used with such a chest tube 10, the guide tube 110 of the clearance device 100 herein described preferably is larger, so as to have a larger inner diameter, for example 30-French or 28-French. However, it is preferable to select chest tubes 10 having the smallest practical diameter while still achieving reliable drainage. Using a clearance device 100 as herein disclosed, it is believed that reliable drainage will be possible due to the ability to reliably clear clot material that might otherwise obstruct the chest-tube passageway 16. As a result, it is contemplated and preferred that smaller chest tubes 10 will be used, for example preferably smaller than 32-French, e.g. 34- to 36- or 38-French. In all cases, the shuttle guide tube 110 preferably has a larger inner diameter than the chest tube 10, preferably at least two French sizes larger. Also preferably, the clearance loop 124a is selected so that its loop diameter substantially corresponds with the inner-wall diameter of the chest tube 10 that is selected.

Figure 10:
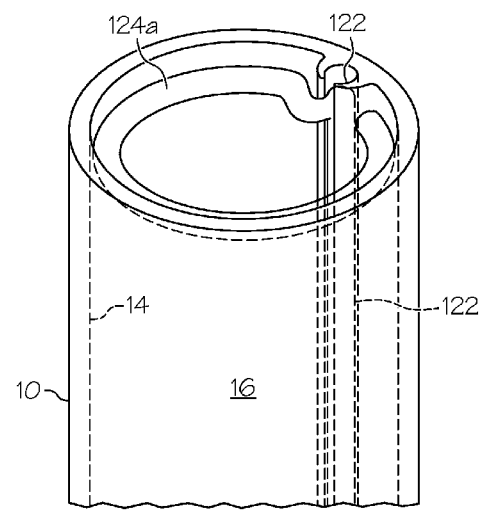
FIG. 10 is a perspective view of the distal region of a medical tube according to a further embodiment hereafter described, which includes a slot disposed in the inner wall of the medical tube that is adapted to house and accommodate the guide wire as it translates along the axis of the medical tube.

In the embodiments already discussed and illustrated in the aforementioned figures, the chest tube 10 has a single inner lumen (defined by inner diameter 14) corresponding to the chest-tube passageway 16, which has a circular cross-section. In a further embodiment illustrated in FIG. 10, the inner surface of the chest tube 10 wall has a substantially circular cross-section but also defines a slot 222 extending longitudinally along the length of the chest tube 10, to accommodate the guide wire 122 therein. The guide wire 122 terminates at its distal end in a modified loop 124a whose shape corresponds substantially to the cross-section of the inner surface of the chest tube 10 wall, having the slot 222 therein. This embodiment may be desirable in applications where the chest tube 10 may undergo relatively sharp bends, so that the slot 222, which houses the guide wire 122, can help prevent buckling of the wire 122 on advancement thereof.

Figure 11:
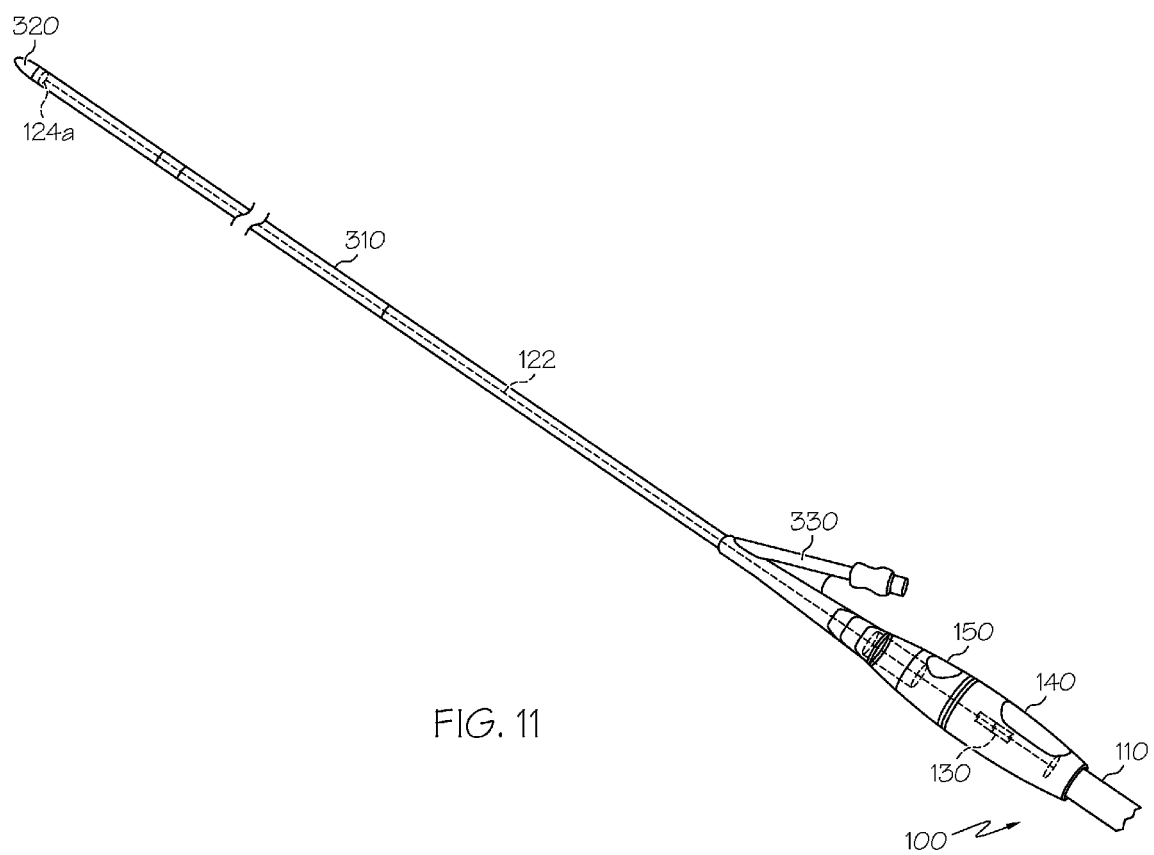
FIG. 11 is a schematic perspective illustration showing a clearance device coupled to a urinary catheter to permit clearance of the catheter of obstructions formed therein.

As noted above, the medical tube need not be a chest tube. The clearance device 100 herein described can be used in conjunction with other medical tubes used to provide fluid communication between a location within a human or animal body and an external apparatus or environment, either to drain fluid or other material from the body (e.g. chest tube, urinary catheter or other drainage tube) or to deliver material from outside the body (e.g. NG-tube or intubation tube). In one such embodiment, shown in FIG. 11, the clearance device 100 is coupled to a urinary catheter 310 to clear the catheter of obstructions that may form therein. Obstructions that may form within a urinary catheter include salt crystals and, in patients with bladder or urinary-tract disease processes, clotted blood. The shuttle guide tube 110 is connected to the proximal end of the catheter 310 similarly as described above, to provide fluid communication between the catheter and guide tube 110. As seen in FIG. 11, a urinary catheter typically has a bullet-type (e.g. domed or conical) cap 320 at its distal end, with a small lumen at its center, to assist in insertion of the catheter 310 into and through the patient's urethra. In addition, it will be appreciated that a urinary catheter typically will have a much smaller diameter than a chest tube or other body drainage tube, or an intubation or feeding tube. The diameter of the shuttle guide tube 110, and all the associated fittings and other components, can be dimensioned appropriately so that the guide tube 110 can be effectively mated in fluid communication with the particular medical tube with which it is to be used. Alternatively, appropriate reducer or expansion fittings may be used to mate otherwise mis-matched medical tube and shuttle guide tube diameters.

Still referring to FIG. 11, the clearance device 100 is used to clear obstructions from the catheter 310, or from any other medical tube, similarly as for the chest tube 10 described above. In a preferred embodiment, the shuttle member 140 is normally advanced and rests against shuttle stop 150 disposed around and near the distal end of the guide tube 110, so that the guide wire 122 is fully advanced within the catheter, and the clearance member 124a normally rests at the catheter's distal end. to clear obstructions from the catheter 310, the shuttle member 140 is drawn proximally along the length of tube 110, causing the guide wire 122 and clearance member 124a to be correspondingly drawn proximally through the catheter 310, to thereby loosen any debris adhered to the catheter inner wall and draw it proximally, out from the catheter 310 and into the guide tube 140. Preferably, the guide tube 140 is connected to a suction source at its proximal end (not shown in FIG. 11), to draw material out. Optionally, and as illustrated in FIG. 11, the catheter may include a lateral channel 330 in communication with and extending from the main catheter lumen, which can be connected to an alternative source of suction, to a Foley collection bag, a pressure transducer to provide real-time pressure data, or other desired apparatus or instrumentation. In a further alternative particularly in the case of a urinary catheter, the lateral channel 330 can be connected in fluid communication with an expandable retainer balloon disposed at the distal end of the catheter as known in the art (not shown), which when inflated acts to retain the distal end of the catheter within the bladder of a patient. In this embodiment, the lateral channel 330 can be used to deliver and withdraw inflation fluid from the retainer balloon, to either place or remove the catheter in/from the bladder.

In addition to use with a catheter, a similar lateral channel (or channels) as seen in FIG. 11 can be provided with any medical tube used for any purpose, where it is desirable to have an additional access port into the medical tube, or into the body cavity where the distal end of the medical tube resides, such as to deliver medication. For example, in one embodiment a medication can be delivered to the patient's body cavity by inserting a smaller catheter through the lateral channel 330 and snaking the smaller catheter up through the catheter 310 (or other medical tube) until it reaches or, if desired, just emerges from the distal end thereof. Then a syringe or other delivery device connected to the proximal end of the smaller catheter can be used to deliver the medication or other fluid through the smaller catheter and into the body cavity where the distal end of the urinary catheter 310 (or other medical tube) has been placed.

Figure 12:
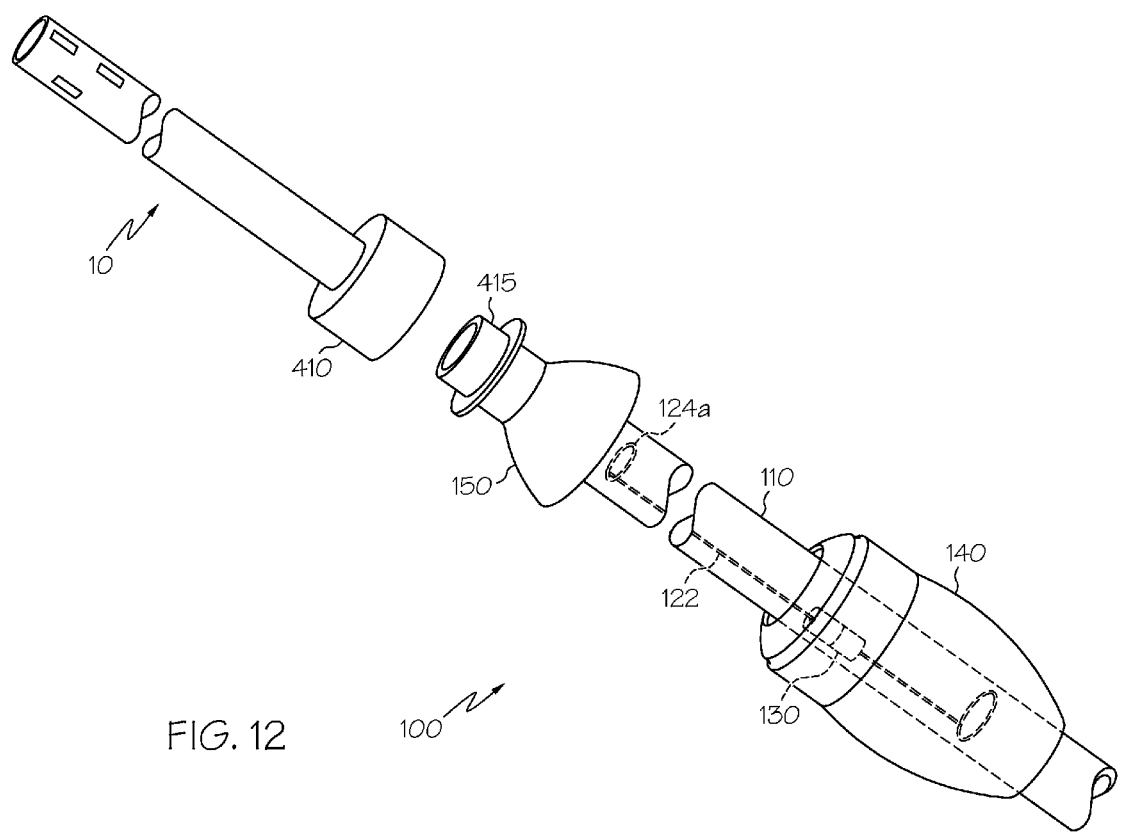
FIG. 12 is a schematic side view of a clearance device and a chest tube, wherein normally-closed mating connectors are provided at the mating ends of the respective chest tube and shuttle guide tube.

The medical tube (e.g. chest tube 10) and/or shuttle guide tube 110 can be provided normally-closed valves or valve connectors 410,415 at their respective mating ends, as seen schematically in FIG. 12. In this embodiment, the clearance device 100 can be removably secured in fluid communication with the chest tube 10, wherein when the guide tube 110 and chest tube 10 are disconnected, their respective ends are sealed via normally-closed valves provided in the respective mating connectors 410,415. Any suitable mating connectors that are normally closed but provide fluid communication through them once mated can be used in this application, provide that the fluid opening through them when mated is large enough to accommodate the clearance member 124 therethrough. Alternative to separate connectors 410,415, the tubes 10 and 110 may be provided directly with normally-closed valves that can be manually actuated once the tubes have been secured in fluid communication. The embodiment described here will be useful to change out an irreversibly blocked guide tube 110 with a fresh guide tube 110 in the unlikely event of such a blockage, without compromising the sterile field within the chest tube 10. Alternatively, this construction will permit intermittent connection of the guide tube 110 to the chest tube, when necessary to clear an obstruction. This can be achieved, for example, by disconnecting the chest tube 10 from the normal suction source (not shown) and connecting it temporarily to the clearance device 100 (guide tube 110) as necessary to clear obstructions. When the clearance operation is complete, the guide tube 110 can be disconnected, and the chest tube 10 re-connected to its normal suction source. In a further alternative, the valves (whether directly in the respective tubes or provided in connectors 410,415, may be manually actuated while the tubes 10 and 110 remain connected, so that when the guide wire and clearance member are fully withdrawn from the chest tube 10, the valves are closed, and when the guide wire and clearance member are advanced within the chest tube 10, the valves are open. In practice, this may be a less preferred embodiment because having the valves normally closed in operation will prevent suction from being applied within the chest tube 10 unless suction is drawn laterally (e.g. through a lateral channel 330 as described previously). In addition, this mode of operation will prevent the clearance member 124 from normally resting at the distal end of the chest tube 10 when not in use, because the valves could not be closed with the guide wire 122 extending through them. Hence, the valves should not be maintained normally closed while the device 100 is in use when it is desired that the clearance member 124 normally rest at the distal end of the chest tube 10.

In an embodiment, a guide wire manipulation device 50 comprises an sonic transducer 52 coupled to an ultrasonic wave guide 54, which in turn is coupled to the wire clearance member 120. In FIG. 2, the wave guide 54 is shown coupled, e.g. by welding or braizing, to the magnetic guide 130. Because the magnetic guide 130, guide wire 122 and clearance member 124 are all in continuous physical contact, sonic vibrations introduced at the wire guide 130 will be transmitted to the clearance member 124. Sonic vibrations generated by the transducer 52 are thus conducted through the guide wire 122 and to the clearance member 124, to induce sonic motion to that member 124 as well as any surrounding fluid, further assisting in the breakup and/or dislodgment of any foreign or obstructing material in the chest tube 10. Alternative to sonic energy, the transducer 52 can impart other forms of energy, such as sub-sonic vibrations, acoustic pulses, or even full or partial (e.g. back-and-forth or 'whipping') rotation to the wave guide 54, which in turn will communicate the associated vibrations, or rotations to the guide wire 122 and ultimately to the clearance member 124 to assist in breaking up any debris. Preferably, the manipulation device 50 is disposed so as not to compromise the sterile environment within the chest tube 10 and guide tube 110 when in use. In the illustrated embodiment, the wave guide 54 exits the proximal end of the guide tube 110 on its way to the transducer 52. The wave guide 54 may then exit the vacuum pathway (between the guide tube 110 and suction source 200) via a lateral fitting or channel, e.g. through a suitable septum (not shown), to be connected to the transducer 52. Because this exit occurs proximate the guide tube 110 relative to the suction pathway, so long as the suction from suction source 200 is maintained while in use, this should not introduce any foreign material into the chest tube 10, or compromise the sterile filed therein. In addition to introducing sonic or sub-sonic vibratory energy to the clearance member 124a, any fluid being conducted through guide lumen 162 also will be subjected to such vibrations, resulting in sonically or sub-sonically excited fluid jets emerging from openings 164, which will further assist in the dislodgment of debris.

Although the invention has been described with respect to certain preferred embodiments, it is to be understood that the invention is not limited by the embodiments herein disclosed, which are exemplary and not limiting in nature, but is to include all modifications and adaptations thereto as would occur to the person having ordinary skill in the art upon reviewing the present disclosure, and as fall within the spirit and the scope of the invention as set forth in the appended claims.

What is claimed is:

1. A device for clearing obstructions from a medical tube, the device comprising a guide tube having an inner diameter, an elongate guide member at least partially disposed in and translatable through said guide tube, and a clearance member in the form of a loop attached to or formed integrally with said guide member said loop having an opening that permits the flow of material through said loop.

2. The device of claim 1, said guide member comprising a guide wire, said loop being formed from or attached to a terminal portion of said guide wire.

3. The device of claim 1, said loop lying in a plane that is at an angle to a longitudinal axis of said guide member at a point where said loop and said guide member intersect.

4. The device of claim 3, said angle being in the range of 75° to 105°.

5. The device of claim 1, further comprising a medical tube having an inner diameter and a proximal end adapted to be coupled to a distal end of said guide tube, said loop having a diameter that substantially corresponds to the inner diameter of said medical tube.

6. The device of claim 5, the inner diameter of said medical tube being smaller than the inner diameter of said guide tube.

7. The device of claim 5, said medical tube proximal end being coupled to said guide tube distal end, said loop being disposed in said medical tube, said loop presenting a substantially unobstructed pathway therethrough for the flow of material from a location in said medical tube distal to said loop to a location in said medical tube proximal to said loop regardless whether said clearance member is being translated or is at rest within said medical tube.

8. The device of claim 1, said guide member being flexible but biased to a straight configuration.

9. The device of claim 1, said guide member being a guide wire comprising a core wire and a sheath wire wound around the core wire to provide a spiral-wound wire sheath.

10. The device of claim 5, said medical tube comprising one or a plurality of apertures through a wall of said medical tube in a distal region thereof, said clearance member being dimensioned and oriented so that it cannot pass through said one or a plurality of apertures.

11. The device of claim 1, further comprising a medical tube coupled to the guide tube's distal end, and a $CO_2$-sensor provided to detect the presence of $CO_2$ in said medical tube.

12. The device of claim 1, further comprising a wire manipulation device effective to deliver energy or motion to the clearance member when in use.

13. The device of claim 1, further comprising a shuttle member disposed outside the guide tube and adapted to translate along a length thereof, and a magnetic guide secured to said guide member, said magnetic guide being adapted to be magnetically coupled to said shuttle member through a wall of said guide tube so that translation of said shuttle member along the length thereof induces a corresponding translation of said guide member.

14. The device of claim 13, said shuttle member comprising a through bore, said guide tube being slidably received through the through bore of said shuttle member to accommodate translation of the shuttle member over said guide tube and along its length.

15. The device of claim 13, further comprising a shuttle stop secured to the guide tube in a distal region thereof, said shuttle member being attachable to said shuttle stop via a reversible mechanical or magnetic attachment.

16. The device of claim 13, further comprising a medical tube having a proximal end adapted to be coupled to a distal end of said guide tube, said guide member having a length between its distal end and said magnetic guide that is substantially equal to the length of said medical tube plus a distance between said shuttle stop and the proximal end of said medical tube when the proximal end of said medical tube is coupled to the distal end of said guide tube.

17. The device of claim 16, said clearance member being disposed at the distal end of said guide member.

18. A device for clearing obstructions from a medical tube, the device comprising a medical tube having an inner diameter, an elongate guide member at least partially disposed in said medical tube, and a clearance member in the form of a loop attached to or formed integrally with said guide member and having a diameter that substantially corresponds to the inner diameter of said medical tube, said loop presenting a substantially unobstructed pathway therethrough for the flow of material from a location in said medical tube distal to said loop to a location in said medical tube proximal to said loop regardless whether said clearance member is being translated or is at rest within said medical tube.

19. The device of claim 18, said guide member comprising a guide wire, said loop being formed from or attached to a terminal portion of said guide wire.

20. The device of claim 18, said loop lying in a plane that is at an angle to a longitudinal axis of said guide member at a point where said loop and said guide member intersect.

21. A method of clearing obstructions from a medical tube, comprising at least partially inserting in said medical tube, through a proximal end thereof, an elongate guide member having a clearance member in the form of a loop attached to or formed integrally with said guide member such that said clearance member is disposed within said medical tube, said loop having a diameter that substantially corresponds to an inner diameter of said medical tube, translating said guide member to correspondingly translate said clearance member within said medical tube to thereby dislodge debris within said medical tube, wherein said loop presents a substantially unobstructed pathway therethrough for the flow of material from a location in said medical tube distal to said loop to a location in said medical tube proximal to said loop regardless whether said clearance member is being translated or is at rest within said medical tube.

22. The method of claim 21, wherein the translation of said guide member and clearance member does not compromise a sterile field in said medical tube.

* * * * *

UNITED STATES PATENT AND TRADEMARK OFFICE
CERTIFICATE OF CORRECTION

| | | |
|---|---|---|
| PATENT NO. | : 8,048,233 B2 | Page 1 of 1 |
| APPLICATION NO. | : 12/915328 | |
| DATED | : November 1, 2011 | |
| INVENTOR(S) | : Edward M. Boyle, Jr. et al. | |

It is certified that error appears in the above-identified patent and that said Letters Patent is hereby corrected as shown below:

At Col. 7, Line 9, replace "2c" with "2D".

At Col. 11, Line 62, insert a --.-- after the word "polyethylene".

At Col. 12, Line 21, delete the word "to" after the word "equal".

At Col. 14, Line 38, replace the word "members" with "member".

At Col. 15, Line 14, delete the word "are".

At Col. 17, Line 6, replace "to" with "To".

At Col. 17, Line 57, replace the word "provide" with "provided".

At Col. 18, Line 10, replace "415," with "415),".

Signed and Sealed this
Thirty-first Day of January, 2012

David J. Kappos
*Director of the United States Patent and Trademark Office*